US008513264B2

(12) United States Patent
Mark et al.

(10) Patent No.: US 8,513,264 B2
(45) Date of Patent: Aug. 20, 2013

(54) COMBINATION THERAPY FOR THE TREATMENT OF DIABETES AND RELATED CONDITIONS

(75) Inventors: Michael Mark, Biberach (DE); Peter Eickelmann, Mittelbiberach (DE); Gerd Luippold, Warthausen-Birkenhard (DE); Leo Thomas, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/062,777

(22) PCT Filed: Sep. 8, 2009

(86) PCT No.: PCT/EP2009/061659
§ 371 (c)(1),
(2), (4) Date: Apr. 6, 2011

(87) PCT Pub. No.: WO2010/029089
PCT Pub. Date: Mar. 18, 2010

(65) Prior Publication Data
US 2011/0263617 A1    Oct. 27, 2011

(30) Foreign Application Priority Data

Sep. 10, 2008    (EP) .................................... 08105293

(51) Int. Cl.
*A61K 31/519*    (2006.01)
(52) U.S. Cl.
USPC .................. 514/262.1; 514/302; 514/256
(58) Field of Classification Search
USPC .................... 514/262.1, 256, 302
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Salvin |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,599,338 A | 7/1986 | Regnier et al. |
| 4,639,436 A | 1/1987 | Junge et al. |
| 4,687,777 A | 8/1987 | Meguro et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,517 A | 9/1991 | Findeisen et al. |
| 5,084,460 A | 1/1992 | Munson, Jr. et al. |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,107,302 A | 8/2000 | Carter et al. |
| 6,166,063 A | 12/2000 | Villhauer |

(Continued)

FOREIGN PATENT DOCUMENTS

| | | |
|---|---|---|
| CA | 1123437 A1 | 5/1982 |
| CA | 2136288 A1 | 5/1995 |

(Continued)

OTHER PUBLICATIONS

Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Abstract in English for German DE2205815, 1972.
Abstract in English for German EP0023032, 1981.
Abstract in English, for KR20070111099, Nov. 11, 2007.
Ahren B: "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

(Continued)

*Primary Examiner* — Rei-tsang Shiao
(74) *Attorney, Agent, or Firm* — Michael P. Morris; Timothy X. Witkowski; David L. Kershner

(57) ABSTRACT

The present invention relates to combinations of DPP-4 inhibitors with GPR119 agonists, as well as to the use of these combinations for treating and/or preventing metabolic diseases, particularly diabetes (especially type 2 diabetes mellitus) and conditions related thereto.

21 Claims, 3 Drawing Sheets

(56) References Cited

U.S. PATENT DOCUMENTS

| | | |
|---|---|---|
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 * | 1/2009 | Eckhardt et al. ............ 514/234.2 |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,645,763 B2 | 1/2010 | Himmelsbach et al. |
| 7,718,666 B2 | 5/2010 | Boehringer et al. |
| 7,799,782 B2 * | 9/2010 | Munson et al. ............ 514/234.5 |
| 7,820,815 B2 | 10/2010 | Pfrengle et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0166125 A1 | 8/2004 | Himmelsbach et al. |
| 2004/0180925 A1 | 9/2004 | Matsuno et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0142310 A1 | 6/2006 | Pfrengle et al. |
| 2006/0154866 A1 | 7/2006 | Chu et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0259900 A1 | 11/2007 | Sieger et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0183531 A1 | 7/2010 | Johncock et al. |
| 2010/0204250 A1 | 8/2010 | Himmelsbach et al. |
| 2011/0046076 A1 | 2/2011 | Eickelmann et al. |

| | | | |
|---|---|---|---|
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |

FOREIGN PATENT DOCUMENTS

| | | |
|---|---|---|
| CA | 2418656 A1 | 2/2002 |
| CA | 2496249 A1 | 3/2004 |
| CA | 2496325 A1 | 3/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1537880 A1 | 6/2005 |
| EP | 1557165 A1 | 7/2005 |
| EP | 1586571 A1 | 10/2005 |
| EP | 1760076 | 3/2007 |
| EP | 1829877 A1 | 9/2007 |
| EP | 1852108 A1 | 11/2007 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| JP | S374895 A | 6/1962 |
| JP | 770120 | 3/1995 |
| JP | 2001213770 | 8/2001 |
| JP | 2003300977 A | 10/2003 |
| JP | 2006045156 A | 2/2006 |
| KR | 20070111099 A | 11/2007 |
| WO | 9107945 A1 | 6/1991 |
| WO | 9205175 A1 | 4/1992 |
| WO | 9402150 A1 | 2/1994 |
| WO | 9403456 A1 | 2/1994 |
| WO | 9609045 A1 | 3/1996 |
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 A1 | 3/1998 |
| WO | 9822464 A1 | 5/1998 |
| WO | 9828007 A1 | 7/1998 |
| WO | 9840069 A2 | 9/1998 |
| WO | 9856406 A1 | 12/1998 |
| WO | 9929695 A1 | 6/1999 |
| WO | 9950248 A1 | 10/1999 |
| WO | 0073307 A2 | 12/2000 |
| WO | 0107441 A1 | 2/2001 |
| WO | 0152825 A2 | 7/2001 |
| WO | 0152852 A1 | 7/2001 |
| WO | 0168646 A1 | 9/2001 |
| WO | 0177110 A1 | 10/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03002531 A2 | 1/2003 |
| WO | 03004496 A1 | 1/2003 |
| WO | 03024965 A2 | 3/2003 |
| WO | 03037327 A1 | 5/2003 |
| WO | 03055881 A1 | 7/2003 |
| WO | 03057200 A2 | 7/2003 |
| WO | 03088900 A2 | 10/2003 |
| WO | 03099279 A1 | 12/2003 |
| WO | 03099836 A1 | 12/2003 |
| WO | 03104229 A1 | 12/2003 |
| WO | 03106428 A1 | 12/2003 |
| WO | 2004011416 A1 | 2/2004 |
| WO | 2004018467 A2 | 3/2004 |
| WO | 2004018468 A2 | 3/2004 |
| WO | 2004028524 A1 | 4/2004 |
| WO | 2004033455 A1 | 4/2004 |
| WO | 2004041820 A1 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004062689 A1 | 7/2004 |
| WO | 2004065380 A | 8/2004 |
| WO | 2004081006 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005012288 A1 | 2/2005 |
| WO | 2005023179 A2 | 3/2005 |

| | | | |
|---|---|---|---|
| WO | 2005049022 A2 | 6/2005 | |
| WO | 2005058901 A1 | 6/2005 | |
| WO | 2005061489 A1 | 7/2005 | |
| WO | 2005082906 A1 | 9/2005 | |
| WO | 2005085246 A1 | 9/2005 | |
| WO | 2005092870 A1 | 10/2005 | |
| WO | 2005092877 A1 | 10/2005 | |
| WO | 2005097798 A | 10/2005 | |
| WO | 2005116000 A1 | 12/2005 | |
| WO | 2005116014 A1 | 12/2005 | |
| WO | 2005117861 A1 | 12/2005 | |
| WO | 2005117948 A1 | 12/2005 | |
| WO | 2006005613 A1 | 1/2006 | |
| WO | 2006029769 A1 | 3/2006 | |
| WO | 2006036664 A1 | 4/2006 | |
| WO | 2006040625 A1 | 4/2006 | |
| WO | 2006047248 A1 | 5/2006 | |
| WO | 2006048209 A1 | 5/2006 | |
| WO | 2006048427 A1 | 5/2006 | |
| WO | 2006068163 A1 | 6/2006 | |
| WO | 2006071078 A1 | 7/2006 | |
| WO | 2006076231 A2 | 7/2006 | |
| WO | 2006083491 A2 | 8/2006 | |
| WO | 2006135693 A2 | 12/2006 | |
| WO | 2006137085 A1 | 12/2006 | |
| WO | 2007007173 A2 | 1/2007 | |
| WO | 2007014886 A1 | 2/2007 | |
| WO | 2007014895 A2 | 2/2007 | |
| WO | 2007017423 A1 | 2/2007 | |
| WO | 2007033350 A1 | 3/2007 | |
| WO | 2007035355 A2 | 3/2007 | |
| WO | 2007035665 A1 | 3/2007 | |
| WO | 2007041053 A2 | 4/2007 | |
| WO | 2007071738 | 6/2007 | |
| WO | 2007072083 A1 | 6/2007 | |
| WO | 2007078726 A2 | 7/2007 | |
| WO | 2007093610 A1 | 8/2007 | |
| WO | 2007099345 A1 | 9/2007 | |
| WO | 2007120702 A2 | 10/2007 | |
| WO | 2007120936 A2 | 10/2007 | |
| WO | 2007128721 A | 11/2007 | |
| WO | 2007128724 A1 | 11/2007 | |
| WO | 2007128761 A2 | 11/2007 | |
| WO | 2007135196 A2 | 11/2007 | |
| WO | 2007137107 A2 | 11/2007 | |
| WO | 2007148185 A2 | 12/2007 | |
| WO | 2007149797 A2 | 12/2007 | |
| WO | 2008005569 A2 | 1/2008 | |
| WO | 2008005576 A1 | 1/2008 | |
| WO | 2008017670 | 2/2008 | |
| WO | 2008022267 A2 | 2/2008 | |
| WO | 2008055870 A1 | 5/2008 | |
| WO | 2008055940 A2 | 5/2008 | |
| WO | 2008070692 A2 | 6/2008 | |
| WO | 2008081205 A1 | 7/2008 | |
| WO | 2008083238 A2 | 7/2008 | |
| WO | 2008087198 A1 | 7/2008 | |
| WO | 2008093878 A1 | 8/2008 | |
| WO | 2008093882 A1 | 8/2008 | |
| WO | 2008113000 A1 | 9/2008 | |
| WO | 2008131149 A2 | 10/2008 | |
| WO | 2009011451 A | 1/2009 | |
| WO | 2009022007 A1 | 2/2009 | |
| WO | 2009022008 A1 | 2/2009 | |
| WO | 2009022010 A1 | 2/2009 | |
| WO | 2009024542 A2 | 2/2009 | |
| WO | 2009063072 A2 | 5/2009 | |
| WO | 2009064399 A1 | 5/2009 | |
| WO | 2009099734 A1 | 8/2009 | |
| WO | 2009121945 A2 | 10/2009 | |
| WO | 2009123992 A1 | 10/2009 | |
| WO | 2009147125 A1 | 12/2009 | |
| WO | 2010015664 A1 | 2/2010 | |
| WO | 2010018217 A2 | 2/2010 | |
| WO | 2010029089 A2 | 3/2010 | |
| WO | 2010043688 A1 | 4/2010 | |
| WO | 2010045656 A2 | 4/2010 | |
| WO | 2010072776 A1 | 7/2010 | |
| WO | 2010079197 A1 | 7/2010 | |
| WO | 2010086411 A1 | 8/2010 | |
| WO | 2010092125 A1 | 8/2010 | |
| WO | 2010092163 A2 | 8/2010 | |
| WO | 2010106457 A2 | 9/2010 | |
| WO | 2010147768 A1 | 12/2010 | |
| WO | 2011039367 A2 | 4/2011 | |
| WO | 2011064352 A1 | 6/2011 | |
| WO | 2011113947 A1 | 9/2011 | |
| WO | 2011138380 A1 | 11/2011 | |
| WO | 2011138421 A1 | 11/2011 | |
| WO | 2011161161 A1 | 12/2011 | |
| WO | 2012065993 A1 | 5/2012 | |

OTHER PUBLICATIONS

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Aulinger, B.A. et al., "Ex-4 and the DPP-IV Inhibitor Vildagliptin have Additive Effects to Suppress Food Intake in Rodents". Abstract No. 1545-P, 2008.

Balaban, Y.H.et al., "Dipeptidyl peptidase IV (DDP IV) in NASH patients" Annals of Hepatology, vol. 6, No. 4, Oct. 1, 2007, pp. 242-250, abstract.

Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Beljean-Leymarie et al., Hydrazines et hydrazones heterocycliques. IV. Syntheses de derives de l'hydrazine dans la serie des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 18-193.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstract. EP412358, 1991:185517, Findeisen.

Chemical Abstract: FR2707641, 1995:543545, Dodey.

Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, (Kiev), vol. 5, 1986, pp. 41-44.

Clinical Trials. "View of NCT00601250 on 1008-01-25: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].

Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.

Clinical Trials. View of NCT00730275 on Aug. 7, 2008. "A study to assess the pharmacokinetics, safety and tolerability of Sitagliptin i adolescents".

Clinical Trials: NCT00602472. "BI 1356 in combination withe metformin and a sulphonylurea in Type 2 Diabetes". DrugLib.com, Nov. 3, 2008.

Clinical Trials: NCT00622284. Efficacy and Safety of BI 1356 in Combination with Metformin in Patients with Type 2 Diabetes. Boehringer Ingelheim Pharmaceuticals, Aug. 2008.

Clinical Trials: NCT00798161. "Safety and efficacy of BI 1356 Plus Metformin in Type 2 Diabetes, Factorial Design". Clinical Trials.gov archive. A Service of the U.S> National Institutes of Health. Nov. 24, 2008, p. 1-3.

Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.

Conarello, S.L. et al., "Mice lacking dipeptidyl peptidase IV are protected against obesity and insulin resistance". PNAS, May 27, 2003, vol. 100, No. 11, p. 6825-6830.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.

DeMeester, I. et al.; "CD26, let it cut or cut it down", Review: Immunology Today; Aug. 1999, vol. 20, No. 8 pp. 367-375.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, pS367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.

Gallwitz, B. et al., "Saxagliptin, a dipeptidase IV inhibitor for the treatment of type 2 diabetes". Drugs, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) vol. 248 pp. 1-59.

Graefe-Mody et al., "The novel DPP-4 inhibitor" Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 1545-1552.

He, Y.L. et al., "The influence of hepatic impariment on the pharmacokinetics f the dipeptidyl peptidase IV (DPP-4) inhibitor vildagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

International Search Report and Written Opinion for PCT/EP2009/061659 mailed Mar. 9, 2010.

Januvia; Patient Information; 2010.

Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

March, J. "Advanced Organic Chemistry: Reactions, Mechanisms, and Structure". Fourth Edition, 1992, pp. 652-653.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Patani George A. et al.: "Bioisoterism : A Rational Approach in Drug Design", Chemical Reviews, 1996, vol. 96, No. 8, pp. 3147-3176.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Pospisilik, et al; Dipeptidyl Peptidase IV Inhibitor Treatment Stimulates ? -Cell Survival and Islet Neogenesis in Streptozotocin-Induced Diabetic Rats; Diabetes, vol. 52, Mar. 2003 pp. 741-750.

Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.

Rhee et al.: "Nitrogen-15-Labeled Deoxynucleosides. 3. Synthesis of [3-15N]-2'-Deoxyadenosine" J. Am. Chem. Soc. 1990, 112, 8174-8175.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Salomon, J., et al; Ultraviolet and g-Ray-lnduced Reactions of Nucleic Acid Constituents. Reactions of Purines with Amines; Photochemistry and Photobiology (1974) vol. 19 pp. 21-27.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Stahl, P.H., "Handbook of Pharmaceutical Salts". C.G. Wermuth, Wiley-VCH, 2002, p. 61.

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Tanaka, S.. et al; "Suppression of Arthritis by the Inhibitors of Dipeptidyl Peptidase IV," In. J. Immunopharmac., vol. 19, No. 1, pp. 15-24, 1997.

Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.

Thomas, Leo et al: "(R)-8-(3-Amino-piperidin-1-yl)-7-but-2-ynyl-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, Apr. 1, 2008, pp. 175-182 abstract p. 177, col. 2, paragraph 1 table 1 p. 1B1, col. 2, last paragraph—p. 182, col. 1.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino)-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IB inhibitor, antidiabetic agent" Drugs of the Future, Prous Science, ES,vol. 33, No. 6, Jun. 1, 208, pp. 473-477.

White, J.R., "Dipeptidyl Peptidase-IV Inhibitors: Phamacological Profile and Clinical Use". Clinical Diabetes, vol. 26, 2008, p. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

Wolff, M.E.: "Burger's Medicinal Chemistry and Drug Discovery" Fifth Edition, vol. 1: Principles and Practice, pp. 975-977, 1994, John Wiley & Sons, Inc.

World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.

Yoshikawa, Seiji et al.: Chemical Abstract of Japanese Patent No. WO 2003/104229 Preparation of purinone derivatives as dipeptidylpeptidase IV (DPP-IV) inhibitors, 2003.

Zejc, Alfred, et al; "Badania Nad Piperazynowymi Pochodnymi Dwumetyloksantyn" Acta Polon Pharm, XXXV (1976) Nr. 4 pp. 417-421.

Zhong, Qing et al; "Glucose-dependent insulinotropic peptide stimulates proliferation and TGF-? release from MG-63 cells," Peptides 24 (2003) 611-616.

Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.

Augusti, D.V. et al., "Quantitative determinatio of the enantiomeric composition of thalidomide solutions by electrospray ionizatio tandem mass spectrometry". Chem Comm, 2002, p. 2242-2243.

Bastin, R.J. et al., "Salt Selection and Optimization Procedures for Pharmaceutical New Chemical Entities". Organic Process Research and Development, 2000, vol. 4, p. 427-435.

Bundgaard, H. "Design of prodrugs: Bioreversible derivatives for various functional groups and chemical entities". Royal Danish School of Pharmacy, 1985, p. 1-92.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Demuth, H-U. et al., "Type 2 diabetes—Therapy with dipeptidyl peptidase IV inhibitors". Biochimica et Biophysica Acta, vol. 1751(1), 2005, p. 33-44.

Gallwitz, B. "Sitagliptin with Metformin: Profile of a Combination for the Treatment of Type 2 Diabetes". Drugs of Today, Oct. 2007, 43(10), p. 681-689.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

Hunziker, D. et al, "Inhibitors of DPP IV—recent advances and structural views", Current Topics in Medicinal Chemistry, 2005, vol. 5 issue 16, pp. 1623-1637.

International Search Report and Written Opinion for PCT/EP2011/054169 mailed Aug. 4, 2011.

International Search Report and Written Opinion for PCT/EP2011/057163 mailed Jun. 27, 2011.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.

Levien,T.L. et al, "New drugs in development for the treatment of diabetes", Diabetes Spectrum, American Diabetes Association, US, vol. 22, No. 2, Jan. 1, 2009, pp. 92-106.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.

Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.

Sune Negre, J. M. "New Galenic Contributions to Administration Forms". Continued Training for Hospital Pharmacists 3.2. [retrieved on Feb. 23, 2011] . Retrieved from the internet <http://www.ub.es/legmh/capitols/sunyenegre.pdf>.

Thomas, L., "Chronic treatment with the Dipeptidyl Peptidase-4 Inhibitor BI 1356[9R)-8-(3-Amino-piperidin-1-yl)-7- but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

X-Ray Diffraction. The United States Pharmacopeia, 2002, USP 25 NF20, p. 2088-2089.

Gallwitz, B. et al., DPP IV inhibitors for the Treatment of Type 2 Diabetes; Diabetes Frontier (2007) vol. 18, No. 6 pp. 636-642.

Hayashi, Michio., "Recipe for Oral Hypoglycemic Agents to Pathological Condition" Pharmacy (2006) vol. 57, No. 9 pp. 2735-2739.

Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.

Kharkevich, D. A., "Educational Literature" Pharmacology (1987) Third Edition, Meditsina Press, Moscow pp. 47-48.

Komori, Kiyoshi., "Treatment of Diabetes in Patients for Whom Metforming Treatment is Not Appropriate" Modern Physician (2008) vol. 27, No. 2 pp. 163-165.

Matsumiya, Teruhiko, et al., "Therapeutic Drugs for Clinicians" Diagnosis and Treatment (2008) vol. 96, No. 2 pp. 389-390.

Shintani, Maki, et al., "Insulin Resistance and Genes" Circulatory Sciences (1997) vol. 17, No. 12 pp. 1186-1188.

Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.

Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

European Search Report for EP 08 15 9141 mailed Apr. 6, 2009 (European counterpart of U.S. Appl. No. 12/143,128).

Hermann, Robert, et al; Lack of Association of PAX4 Gene with Type 1 Diabetes in the Hungarian Populations; Diabetes (2005) vol. 54 pp. 2816-2819.

International Search Report and Written Opinion for PCT/EP2011/057256 mailed Jul. 22, 2011.

International Search Report and Written Opinion for PCT/EP2012/063852 mailed Sep. 6, 2012.

International Search Report for PCT/EP03/12821 mailed Mar. 30, 2004.

International Search Report for PCT/EP03/13648 mailed Apr. 5, 2004.

International Search Report for PCT/EP2007/058181 mailed Nov. 28, 2007.

Kibbe, Editor. Handbook of Pharmaceuticals Excipiets, Third Edition, Copovidon—pp. 196-197, Date of Revision: Dec. 16, 2008. Mannitol—pp. 424-425, Date of Revision: Feb. 19, 2009.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

Shanks, N. et al., Are animal models predictive for humans?, PEHM, Philosophy, Ethics, and Humanaities in Medicine, 4(2), 2009, 1-20.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, pA143.

* cited by examiner

COMBINATION THERAPY FOR THE TREATMENT OF DIABETES AND RELATED CONDITIONS

The present invention relates to combinations of certain DPP-4 inhibitors with GPR119 agonists, as well as to the use of these combinations for treating and/or preventing metabolic diseases, particularly diabetes (especially type 2 diabetes mellitus) and conditions related thereto. Pharmaceutical compositions comprising a DPP-4 inhibitor and a GPR119 agonist, each as defined herein, are also contemplated.

Diabetes mellitus is a serious metabolic disease afflicting over 100 million people worldwide. In the United States, there are more than 12 million diabetics, with 600,000 new cases diagnosed each year. It is increasingly prevalent due to a high frequency of complications which leads to a significant reduction of life quality and expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a two to five fold increase in cardiovascular disease risk.

The UKPDS (United Kingdom Prospective Diabetes Study) demonstrated that intensive treatment with current therapeutic drugs, e.g. metformin, sulfonylureas or insulin resulted in only a limited improvement of glycemic control (difference in HbA1c ~0.9%). In addition, even in patients within the intensive treatment arm glycemic control deteriorated significantly over time and this was attributed to deterioration of β-cell function. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of leading causes of death worldwide.

Therefore there is an unmet medical need for drugs with a good efficacy with regard to glycemic control, with regard to disease-modifying properties and with regard to reduction of cardiovascular morbidity and mortality while at the same time showing an improved safety profile.

Obesity is the result of an imbalance between caloric intake and energy expenditure. It is highly correlated with insulin resistance and diabetes. However, the molecular mechanisms that are involved in obesity-diabetes syndromes are not clear. During early development of obesity, increased insulin secretion balances insulin resistance and protects patients from hyperglycemia, but after several decades, [beta] cell function deteriorates and non-insulin-dependent diabetes develops in about 20% of the obese population. Obesity has thus become the leading risk factor for diabetes, however, the factors which predispose a fraction of patients to alteration of insulin secretion in response to fat accumulation remain currently unknown. Obesity considerably increases the risk of developing cardiovascular diseases as well. Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails.

GPR119 is a Gs-protein-coupled receptor, predominantly expressed in the pancreatic beta-cells and L-cells of the gut. Activation of the receptor stimulates the cAMP signalling pathway as GLP-1R agonists do. Therefore, an improvement of beta-cell function and beta-cell mass can be expected for an GPR119 agonist. In fact, GPR119 activation stimulates insulin secretion in a glucose dependent manner in-vitro and in-vivo (rodents). It has been shown recently that GPR119 agonists efficiently lower blood glucose in diabetic rodents without risk of hypoglycaemia. Additional GPR119 expression was observed in the gastrointestinal tract and in the rodent, but not human brain. It could be shown that activation of GPR119 in neuroendocrine cells of the gut stimulates GLP-1 release, therefore activation of GPR119 will combine a direct effect on beta-cells with an indirect glucoregulatory effect via intestinal increase of GLP-1 release. Therefore, a therapeutic benefit of GPR119 agonists can be expected in metabolic disorders.

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses, particularly their uses in metabolic (especially diabetic) diseases, are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769 or WO2007/014886; or in WO 2004/050658, WO 2004/111051, WO 2005/058901 or WO 2005/097798; or in WO 2006/068163, WO 2007/071738 or WO 2008/017670; or in WO 2007/128721 or WO 2007/128761.

As further DPP-4 inhibitors the following compounds can be mentioned:

Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine,

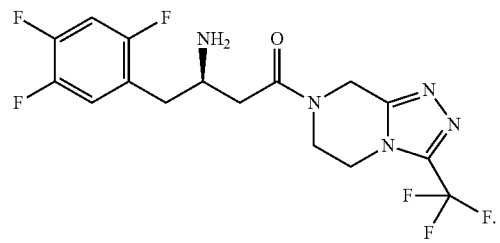

(A)

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485.

For details, e.g. on a process to manufacture, to formulate or to use this compound or a salt thereof, reference is thus made to these documents.

A tablet formulation for sitagliptin is commercially available under the trade name Januvia®. A tablet formulation for sitagliptin/metformin combination is commercially available under the trade name Janumet®.

Vildagliptin (LAF-237) having the structural formula B below is (2S)-{[(3-hydroxyadamantan-1-yl)amino]acetyl}pyrrolidine-2-carbonitrile, also named (S)-1-[(3-hydroxy-1-adamantyl)amino]acetyl-2-cyano-pyrrolidine,

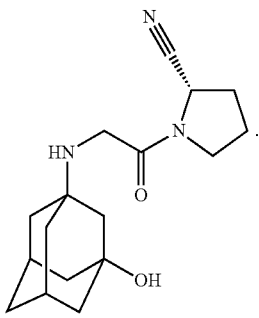

(B)

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723.

For details, e.g. on a process to manufacture, to formulate or to use this compound or a salt thereof, reference is thus made to these documents.

A tablet formulation for vildagliptin is expected to be commercially available under the trade name Galvus®. A tablet formulation for vildagliptin/metformin combination is commercially available under the trade name Eucreas®.

Saxagliptin (BMS-477118) having the structural formula C below is (1S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile,

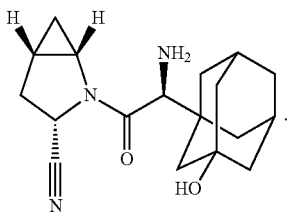

(C)

Saxagliptin is specifically disclosed in U.S. Pat. No. 6,395,767 and in Example 60 of WO 01/68603.

In one embodiment, saxagliptin is in the form of its HCl salt or its mono-benzoate salt as disclosed in WO 2004/052850. In a further embodiment, saxagliptin is in the form of the free base. In a yet further embodiment, saxagliptin is in the form of the monohydrate of the free base as disclosed in WO 2004/052850. Crystalline forms of the HCl salt and the free base of saxagliptin are disclosed in WO 2008/131149. A process for preparing saxagliptin is also disclosed in WO 2005/106011 and WO 2005/115982. Saxagliptin can be formulated in a tablet as described in WO 2005/117841.

For details, e.g. on a process to manufacture, to formulate or to use this compound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl)benzonitrile

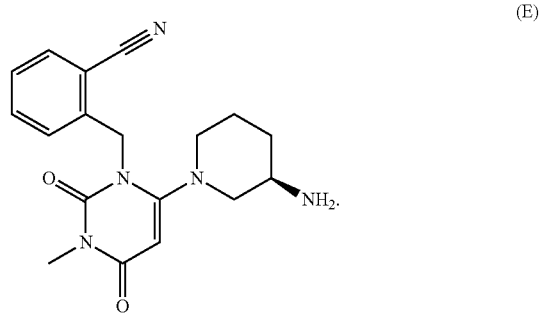 [SMILES: Cn1c(=O)cc(N2CCC[C@@H](N)C2)n(Cc2ccccc2C#N)c1=O]

(E)

Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629. Alogliptin (namely its benzoate salt) can be formulated in a tablet and administered as described in WO 2007/033266. Formulations of aloglipitin with metformin or pioglitazone are described in WO 2008/093882 or WO 2009/011451, respectively. For details, e.g. on a process to manufacture, to formulate or to use this compound or a salt thereof, reference is thus made to these documents.

(2S)-1-{[2-(5-Methyl-2-phenyl-oxazol-4-yl)-ethylamino]-acetyl}-pyrrolidine-2-carbonitrile or a pharmaceutically acceptable salt thereof, preferably the mesylate, or (2S)-1-{[1,1,-Dimethyl-3-(4-pyridin-3-yl-imidazol-1-yl)-propylamino]-acetyl}-pyrrolidine-2-carbonitrile or a pharmaceutically acceptable salt thereof:

These compounds and methods for their preparation are disclosed in WO 03/037327. The mesylate salt of the former compound as well as crystalline polymorphs thereof are disclosed in WO 2006/100181. The fumarate salt of the latter compound as well as crystalline polymorphs thereof are disclosed in WO 2007/071576. These compounds can be formulated in a pharmaceutical composition as described in WO 2007/017423.

For details, e.g. on a process to manufacture, to formulate or to use these compounds or salts thereof, reference is thus made to these documents.

(S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one or a pharmaceutically acceptable salt thereof:

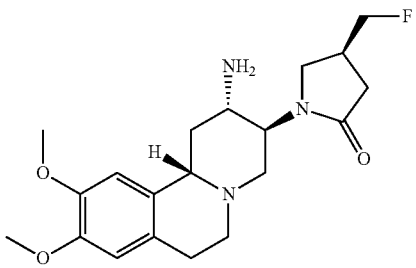 [SMILES: COc1cc2c(cc1OC)[C@@H]1C[C@H](N)[C@@H](N3C[C@@H](CF)CC3=O)CN1CC2]

This compound and methods for its preparation are disclosed in WO 2005/000848. A process for preparing this compound (specifically its dihydrochloride salt) is also disclosed in WO 2008/031749, WO 2008/031750 and WO 2008/055814. This compound can be formulated in a pharmaceutical composition as described in WO 2007/017423. For details, e.g. on a process to manufacture, to formulate or to use this compound or a salt thereof, reference is thus made to these documents.

(3,3-Difluoropyrrolidin-1-yl)-((2S,4S)-4-(4-(pyrimidin-2-yl)piperazin-1-yl)pyrrolidin-2-yl)methanone (also named gosogliptin) or a pharmaceutically acceptable salt thereof:

This compound and methods for its preparation are disclosed in WO 2005/116014 and U.S. Pat. No. 7,291,618.

For details, e.g. on a process to manufacture, to formulate or to use this compound or a salt thereof, reference is thus made to these documents.

(1((3S,4S)-4-amino-1-(4-(3,3-difluoropyrrolidin-1-yl)-1,3,5-triazin-2-yl)pyrrolidin-3-yl)-5,5-difluoropiperidin-2-one or a pharmaceutically acceptable salt thereof:

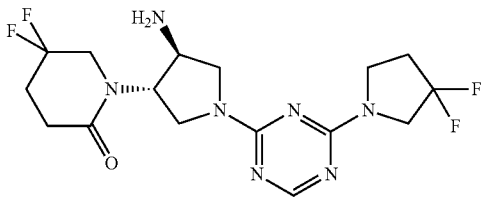 [SMILES: N[C@H]1CN(c2ncnc(N3CCC(F)(F)C3)n2)C[C@@H]1N1CC(F)(F)CCC1=O]

This compound and methods for its preparation are disclosed in WO 2007/148185 and US 20070299076. For details, e.g. on a process to manufacture, to formulate or to use this compound or a salt thereof, reference is thus made to these documents.

(2S,4S)-1-{2-[(3S,1R)-3-(1H-1,2,4-Triazol-1-ylmethyl)cyclopentylamino]acetyl}-4-fluoropyrrolidine-2-carbonitrile or a pharmaceutically acceptable salt thereof:

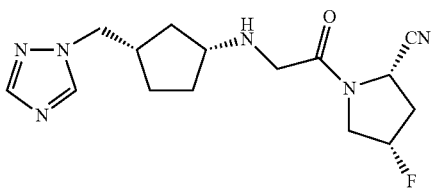 [SMILES: N#C[C@@H]1C[C@H](F)CN1C(=O)CN[C@@H]1CC[C@H](Cn2cncn2)C1]

This compound and methods for its preparation are disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-benzonitrile or a pharmaceutically acceptable salt thereof:

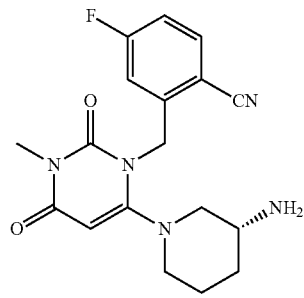 [SMILES: Cn1c(=O)cc(N2CCC[C@@H](N)C2)n(Cc2cc(F)ccc2C#N)c1=O]

This compound and methods for its preparation and use are disclosed in WO 2005/095381, US 2007060530, WO 2007/033350, WO 2007/035629, WO 2007/074884, WO 2007/112368 and WO 2008/033851. Specifically claimed salts include the succinate (WO 2008/067465), benzoate, benzenesulfonate, p-toluenesulfonate, (R)-mandelate and hydrochloride. For details, e.g. on a process to manufacture, to formulate or to use this compound or a salt thereof, reference is thus made to these documents.

5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide or a pharmaceutically acceptable salt thereof:

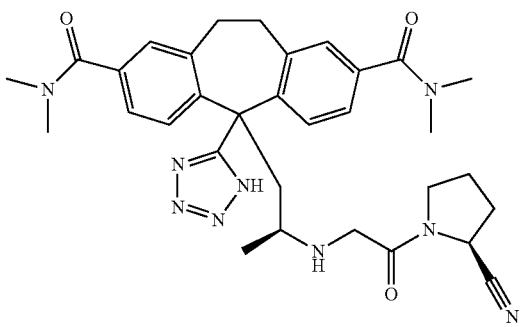 [SMILES: C[C@@H](CC1(c2nnn[nH]2)c2ccc(C(=O)N(C)C)cc2CCc2cc(C(=O)N(C)C)ccc21)NCC(=O)N1CCC[C@H]1C#N]

This compound and methods for its preparation are disclosed in WO 2006/116157 and US 2006/270701. For details, e.g. on a process to manufacture, to formulate or to use this compound or a salt thereof, reference is thus made to these documents.

3-{(2S,4S)-4-[4-(3-Methyl-1-phenyl-1H-pyrazol-5-yl)piperazin-1-yl]pyrrolidin-2-ylcarbonyl}thiazolidine (also named teneligliptin) or a pharmaceutically acceptable salt thereof:

This compound and methods for its preparation are disclosed in WO 02/14271. Specific salts are disclosed in WO 2006/088129 and WO 2006/118127 (including hydrochloride, hydrobromide, inter alia). Combination therapy using this compound is described in WO 2006/129785. For details, e.g. on a process to manufacture, to formulate or to use this compound or a salt thereof, reference is thus made to these documents.

[(2R)-1-{[(3R)-pyrrolidin-3-ylamino]acetyl}pyrrolidin-2-yl]boronic acid (also named dutogliptin) or a pharmaceutically acceptable salt thereof:

This compound and methods for its preparation are disclosed in WO 2005/047297, WO 2008/109681 and WO 2009/009751. Specific salts are disclosed in WO 2008/027273 (including citrate, tartrate). A formulation of this compound is described in WO 2008/144730. For details, e.g. on a process to manufacture, to formulate or to use this compound or a salt thereof, reference is thus made to these documents.

(2S,4S)-1-[2-[(4-ethoxycarbonylbicyclo[2.2.2]oct-1-yl)amino]acetyl]-4-fluoropyrrolidine-2-carbonitrile or a pharmaceutically acceptable salt thereof:

This compound and methods for its preparation are disclosed in WO 2005/075421, US 2008/146818 and WO 2008/114857. For details, e.g. on a process to manufacture, to formulate or to use this compound or a salt thereof, reference is thus made to these documents.

2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile or a pharmaceutically acceptable salt thereof, or 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione or a pharmaceutically acceptable salt thereof:

These compounds and methods for their preparation are disclosed in WO 2009/084497 and WO 2006/068163, respectively. For details, e.g. on a process to manufacture, to formulate or to use these compounds or salts thereof, reference is thus made to these documents.

GPR119 agonists are known in the art. In the following reference is made to representatives of GPR119 agonists:

GPR119 agonists are generically and specifically disclosed for example in the following documents, to which generic and specific reference is made in each case:

WO 2005/061489, e.g. the compounds as defined in any one of claims 1-17, especially any of the compounds disclosed as Examples 1, 3 to 8, 10 to 13, 16 to 50, and 52 to 149 (including those of Tables 1-12), particularly those compounds of formula Id according to claim 16 and of formula Ie according to claim 17.

WO 2006/067531, e.g., the compounds as defined in any one of claims 1-15, especially any of the compounds disclosed as Examples 1 to 136 (including those of Tables 1-14), particularly those compounds of formula Ia according to claim 14.

WO 2006/067532, e.g. the compounds as defined in any one of claims 1-18, especially any of the compounds disclosed as Examples 1 to 149 (including those of Tables 1-10), particularly those compounds of formula Ia according to claim 17.

WO 2006/070208, e.g. the compounds as defined in any one of claims 1-15, especially any of the compounds disclosed as Examples 1 to 3.

WO 2007/003960, e.g. the compounds as defined in any one of claims 1-20, especially any of the oxadiazoles disclosed as Examples 1-238 (including those of Tables 3-8), particularly those compounds of formula Ib according to claim 20, WO 2007/003961, e.g. the compounds as defined in any one of claims 1-16, especially any of the compounds disclosed as Examples 1-44, WO 2007/003962, e.g. the compounds as defined in any one of claims 1-18, especially any of the compounds disclosed as Examples 1-265 (including those of Tables 3-23), particularly those compounds of formula Ic according to claim 18

WO 2007/003964, e.g. the compounds as defined in any one of claims 1-8, especially any of the compounds disclosed as Examples 1-89 (including those of Tables 1-8), particularly those compounds of formula Ib according to claim 8

WO 2007/116229, e.g. the compounds as defined in any one of claims 1-19, especially any of the oxadiazoles disclosed as Examples 1-46 (including those of Tables 3 and 4).

WO 2007/116230, e.g. the compounds as defined in any one of claims 1-33, especially any of the compounds disclosed as Examples 1-62.

WO 2009/034388, e.g. the compounds as defined in any one of claims 1-12 and 17, especially any of those species listed therein in claim 12.

WO 2009/050522, e.g. the compounds as defined in any one of claims 1-13, especially any of the compounds disclosed therein as Examples 1-42 (including those of Tables 1-4).

WO 2009/050523, e.g. the compounds as defined in any one of claims 1-37, especially any of the compounds disclosed therein as Examples 1-54 (including those of Tables 1-7).

WO 2008/083238, e.g. the compounds as defined in any one of claims 1-48, especially any of the compounds disclosed therein as Examples 1-210 (including those of Tables 1-5), particularly Example 52, i.e. 5-ethyl-2-{4-[4-(4-tetrazol-1-yl-phenoxymethyl)-thiazol-2-yl]-piperidin-1-yl}-pyrimidine or a pharmaceutically salt thereof.

WO 2009/014910, e.g. the compounds as defined in any one of claims 1-23, especially any of the compounds disclosed therein as Examples 1-113 (including those of Tables 1 and 2), e.g. Compound 1.

WO 2008/076243, e.g. the compounds as defined in any one of claims 1-14 (including any of those species listed in claim 14), especially the bipiperidines disclosed as Examples 1.1-1.38 of Table 1, Examples 2.1-2.20 of Table 2, Examples 3.1-3.9 of Table 3, Examples 4.1-4.10 of Table 4, Examples 5.1-5.7 of Table 5, Examples 6.1-6.4 of Table 6, Examples 7.1 and 7.2 of Table 7, Examples 8-1-8.3 of Table 8, Examples 10.1 and 10.2 of Table 10, Examples 11.1-11.15 of Table 11, Examples 12.1-12.31 of Table 12, and Examples 13.1-13.27 of Table 13, particularly any compound according to claim 14.

WO 2008/085316, e.g. the compounds as defined in any one of claims 1-14 (including any of those species listed in claim 14), especially the bipiperidines disclosed as Examples 1.1-1.38 of Table 1, Examples 2.1-2.20 of Table 2, Examples 3.1-3.9 of Table 3, Examples 4.1-4.10 of Table 4, Examples 5.1-5.7 of Table 5, Examples 6.1-6.4 of Table 6, Examples 7.1 and 7.2 of Table 7, Examples 8-1-8.3 of Table 8, Examples 10.1 and 10.2 of Table 10, Examples 11.1-11.15 of Table 11, Examples 12.1-12.31 of Table 12, Examples 13.28-13.36, Examples 14.1-14.35, Examples 15.1-15.8 of Table 15, Examples 16.1-16.11 of Table 16, Examples 17.1-17.5 of Table 17, Examples 18.1-18.48 of Table 18, Examples 19.1-19.39 of Table 19, particularly any compound according to claim 14 (including the table-listed compounds).

WO 2008/008887, e.g. the compounds as defined in any one of claims 1-24 (including any of those species listed in claim 24), especially the pyrrolopyrimidines disclosed as Examples 1-151 (including Example 1), particularly any compound according to claim 24.

WO 2008/008895, e.g. the pyrrolopyrimidines disclosed as Examples 1-151 (including Example 1).

WO 2008/070692, e.g. the compounds as defined in any one of claims 1-22 (including any of those species listed in claims 21 and 22), especially the compounds disclosed as Examples 1-192 (including Examples 77 and 83), particularly any compound according to claim 21 and any compound according to claim 22.

WO 2008/097428, e.g. the compounds as defined in any one of claims 1-21 (including any of those species listed in claims 6, 11, 16 and 21), especially the compounds disclosed as Examples 1-272 (including those of Table 1).

WO 2008/109702, e.g. the compounds as defined in any one of claims 1-7 (including any one of those species listed in claim 7, especially the compounds disclosed as Examples 1-17 (including those of Table 1, 2 and 3).

WO 2009/038974, e.g. the compounds as defined in any one of claims 1-6 (including any one of those species listed in claim 6, especially the compounds disclosed as Examples (including Compound A3, C2, D2, E3, E9, G1, G4, H3, I1, J7, J22, K3, O9, O41, P13, T1, U5 and V5).

WO 2009/105715, e.g. the compounds as defined in any one of claims 1-6 (including any one of those species listed in claim 6, especially the compounds disclosed as Examples (including any compound selected from Examples 1 to 20).

WO 2009/105717, e.g. the compounds as defined in any one of claims 1-6 (including any one of those species listed in claim 6, especially the compounds disclosed as Examples (including those of Table 1, 2, 3 and 4, particularly any compound selected from Examples A1 to A9, B1 to B4, C1, D1 to D9, E1, G1 to G18, H1, I1, and J1 to J3, particularly any one of D1 to D9).

WO 2009/105722, e.g. the compounds as defined in any one of claims 1-6 (including any one of those species listed in claim 6, especially the compounds disclosed as Examples (including those of Table 1, 2 and 3, particularly any compound selected from Examples A1 to A32, B1 to B12, and C1 to C3).

WO 2009/106561, e.g. the compounds as defined in any one of claims 1-13 (including any one of those species listed in claim 13, especially the compounds disclosed as Examples (including any compound selected from Examples 1 to 109).

WO 2009/106565, e.g. the compounds as defined in any one of claims 1-12 (including any one of those species listed in claim 12, especially the compounds disclosed as Examples (including any compound selected from Examples 1 to 20).

WO 2008/033431, e.g. the spirocyclic azetidinone compounds as defined in any one of claims 1-22, particularly any of those species listed in claim 22.

WO 2008/033460, e.g. the spiro(azetidine-piperidine) compounds defined by Tables 1, 2, 3a, 3b, 3c, 3d and 4a, preferably any compound selected from the group consisting of the compounds in Tables 5, 6, 7 and 8.

WO 2008/130581, e.g. the pyrimidinone compounds as defined in any one of claims 1-35, particularly any of those species listed in claim 35.

WO 2008/130584, e.g. the pyrimidinone compounds as defined in any one of claims 1-38, particularly any of those species listed in claim 38.

WO 2008/130615, e.g. the tetrahydropyridopyrimidinone compounds of Formula I as defined by "X" in Tables A-D.

WO 2009/055331, e.g. the compounds as defined in any one of claims 1-97, particularly any one of those compounds numbered 1-611, especially any of the species singly claimed in claims 77-97.

WO 2008/025798, e.g. the compounds as defined in any one of claims 1-25 (including any of those species listed in claim 25), especially the compounds disclosed as Examples A1-A48, Examples B1-B108 and Examples C1-C4 (including Examples A2, A39 and B2), particularly any compound according to claim 25.

WO 2008/025799, e.g. the compounds as defined in any one of claims 1-11 (including any of those species listed in claim 11), especially the compounds disclosed as Examples A1-A4, particularly any compound according to claim 11 (including Examples A1 and A4).

WO 2008/025800, e.g. the compounds as defined in any one of claims 1-20 (including any of those species listed in claim 20), especially the compounds disclosed as Examples A1-A22, B1 and B2 (including Examples A2, A22 and B1), particularly any compound according to claim 20.

WO 2004/065380, e.g. the compounds as defined in any one of claims 1-77 (including any of those species listed in claims 73, 74, 75, 76 and 77), especially the compounds disclosed by way of example as, e.g. the Compounds A1-A165, Compounds B1-B139, Compounds C1-C27, Compounds D1-D6 and Compound E1 (including Compounds A124, B70 and B84), particularly any compound according to claims 73-77.

WO 2004/076413, e.g. the compounds as defined in any one of claims 1-47 (including any of those species listed in claims 43, 44, 45, 46 and 47), especially the compounds disclosed by way of example, e.g. the Compounds A1-A60 and Compounds B1-B9 (including Compounds A30, A51 and A52), particularly any compound according to claims 43-47.

WO 2005/007647, e.g. the compounds as defined in any one of claims 1-64 (including any of those species listed in claims 55, 56, 57, 58, 59, 60, 61, 62, 63 and 64), especially the compounds disclosed by way of example, e.g. the Compounds A1-A120, Compounds B1-B5, Compounds C1-C240 and Compounds D1, D2 and E1 (including Compounds A1, A34, A35, A78, A88, A118, A11, A14, A24, A27, A32, A39, A90 and B4), particularly any compound according to claims 55-64.

WO 2005/007658, e.g. the compounds as defined in any one of claims 1-55 (including any of those species listed in claims 42, 43, 44, 45, 46, 47, 48, 49, 50, 51, 52, 53, 54 and 55), especially the compounds disclosed by way of example, e.g. in Tables A to K (including Compounds A5, B5, C1, A194, A214 and D4), particularly any compound according to claims 42-55.

WO 2005/121121, e.g. the compounds as defined in any one of claims 1-34 (including any of those species listed in claims 22, 23, 24 and 33), especially the compounds disclosed by way of example, e.g. the Compounds A1-A122 and Compounds B1-B157 (including Compounds B3, B124, B16, B21 and B143), particularly any compound according to claims 22-24 and 33.

WO 2006/076243, e.g. the compounds of formula I as defined in claim 1, especially the compounds disclosed by way of example, e.g. the Compound 5.

US 2007/0078150, e.g. the compounds of formula Ia and IIa-Iii as defined therein, especially the compounds disclosed by way of example, e.g. the Compounds I-103, and, particularly, the compound as defined in claim 1, i.e. 4-[6-(6-methanesulfonyl-2-methyl-pyridin-3-ylamino)-5-methoxy-pyrimidin-4-yloxy]-piperidine-1-carboxylic acid isopropyl ester.

WO 2006/083491, e.g. the compounds as defined in any one of claims 1-42 (including any of those species listed in claims 40, 41 and 42), especially the compounds disclosed by way of example, e.g. the Compounds 1-103 (including Compounds 75, 10, 24 and 76), particularly any compound according to claims 40 to 42.

WO 2008/137435, e.g. the compounds as defined in any one of claims 1-13, particularly any of those species listed in claim 13.

WO 2008/137436, e.g. the compounds as defined in any one of claims 1-12, particularly any of those species listed in claim 12.

WO 2009/012275, e.g. the pyridone compounds as defined in any one of claims 1-15, particularly any of those species listed in claim 15.

WO 2009/012277, e.g. the compounds as defined in any one of claims 1-15, 18 and 19, particularly any of those species listed in claim 19, especially the pyridone compounds disclosed as Examples 1-4.

In addition, reference is also made to those GPR119 agonists which are mentioned in WO 2007/120689, WO 2007/120702, WO 2007/138362, JP2004269468, JP2004269469, WO 2002/044362 and WO 2003/026661.

In further addition, reference is made to those GPR119 agonists which are mentioned in WO 2006/076231 (the combination WO 2006/076231 concerns combination of a DPP-4 inhibitor with a GPR119 agonist):

Thus, reference is made to a GPR119 agonist of Formula (I) as defined in WO 2006/076231 (cf GPR119 agonists disclosed in WO 2004/065380).

Reference is made to a GPR119 agonist of Formula (II) as defined in WO 2006/076231 (cf GPR119 agonists disclosed in WO 2004/076413).

Reference is made to a GPR119 agonist of Formula (III) as defined in WO 2006/076231 (cf GPR119 agonists disclosed in WO 2005/007647).

Reference is made to a GPR119 agonist of Formula (IV) as defined in WO 2006/076231 (cf GPR119 agonists disclosed in WO 2005/007658).

Reference is made to a GPR119 agonist of Formula (V) as defined in WO 2006/076231 (cf GPR119 agonists disclosed in U.S. 60/577,354, WO 2005/121121).

Reference is made to a GPR119 agonist of Formula (VI) as defined in WO 2006/076231 (cf GPR119 agonists disclosed in WO 2005/061489).

Also reference is made to a GPR119 agonist which is selected from Group A1, Group B1, Group B2, Group B3, Group B4, Group B5, Group C1, Group C2, Group C3, Group C4, Group C5, Group C6, Group C7, Group C8, Group C9, Group 010, Group D1, Group D2, Group D3, Group D4, Group D5, Group D6, Group D7, Group D8, Group D9, Group D10, Group D11, Group D12, Group D13, Group D14, Group E1, Group E2 or Group F1, each as defined in WO 2006/076231.

Also reference is made to a GPR119 agonist which is selected from the left column of Table B as disclosed in WO 2006/076231.

Further reference is made to those GPR119 agonists which are mentioned in WO 2008/005569 as Compound A, i.e. 4-[1-(2-fluoro-4-methanesulfonyl-phenyl)-1H-pyrazolo[3,4-d]pyrimidin-4-yloxy]-piperidine-1-carboxylic acid isopropyl ester (that is described in the genus found in WO 2005/007658), as Compound B, i.e. (2-fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine (that is described in the genus found in WO 2005/007647), as Compound C, i.e. 4-[6-(6-methanesulfonyl-2-methyl-pyridin-3-ylamino)-5-methoxy-pyrimidin-4-yloxy]-piperidine-1-carboxylic acid isopropyl ester (that is described in the genus found in WO 2006/083491), as Compound D, i.e. 4-[6-(6-methanesulfonyl-4-methyl-pyridin-3-ylamino)-5-methoxy-pyrimidin-4-yloxy]-piperidine-1-carboxylic acid isopropyl ester (that is described in the genus found in WO 2006/083491), Compound E, i.e. 4-[6-(6-methanesulfonyl-2-methyl-pyridin-3-ylamino)-5-methyl-pyrimidin-4-yloxy]-piperidine-1-carboxylic acid isopropyl ester (that is described in the genus found in WO 2005/007647 or in Example 3.5 of WO 2008/005576), as Compound F that is described in the genus found in WO 2004/065380, and/or as Compound G, i.e. {6-[1-(3-isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine (that is described in the genus found in WO 2006/083491).

Particular reference is made to those GPR119 agonists of formula (I) as defined in WO 2008/081204, e.g. the compounds as defined in any one of claims 1-13, especially any of the compounds disclosed therein as Examples 1-33 (including those of Tables 1-5).

Particular reference is made to those GPR119 agonists of formula (I) as defined in WO 2008/081205, e.g. the compounds as defined in any one of claims 1-20, especially any of the compounds disclosed therein as Examples 1-46 (including those of Tables 1-3).

Particular reference is made to those GPR119 agonists of formula (I) as defined in WO 2008/081206, e.g. the compounds as defined in any one of claims 1-14, especially any of the compounds disclosed therein as Examples 1-4, i.e. 4-[3-(3-Fluoro-4-methanesulfonylmethylphenoxy)propyl]-1-(5-isopropyl-[1,2,4]oxadiazol-3-yl)piperidine, 4-[3-(3-Fluoro-4-methanesulfonylmethylphenoxy)propyl]-1-(3-isopropyl-[1,2,4]oxadiazol-5-yl)piperidine, 4-[(R)-3-(3-Fluoro-4-methanesulfonylmethylphenoxy)-1-methylpropyl]-1-(5-isopropyl-[1,2,4]oxadiazol-3-yl)piperidine or 1-(3-tert-Butyl-[1,2,4]oxadiazol-5-yl)-4-[3-(3-fluoro-4-methanesulfonylmethyl-phenoxy)propyl]piperidine.

Particular reference is made to those GPR119 agonists of formula (I) as defined in WO 2008/081207, e.g. the compounds as defined in any one of claims 1-15, especially any of the compounds disclosed therein as Examples 1-22 (including those of Tables 1 and 2).

Particular reference is made to those GPR119 agonists of formula (I) as defined in WO 2008/081208, e.g. the compounds as defined in any one of claims 1-16, especially any of the compounds disclosed therein as Examples 1-4.

Particular reference is made to that GPR119 agonist of formula (I) disclosed in WO 2008/083238 as Example 52, i.e. 5-ethyl-2-{4-[4-(4-tetrazol-1-yl-phenoxymethyl)-thiazol-2-yl]-piperidin-1-yl}-pyrimidine or a pharmaceutically salt thereof.

Particular reference is made to that GPR119 agonist of Formula (I) as shown in WO 2007/035355, i.e. 4-[5-methyl-6-(2-methyl-pyridin-3-yloxy)-pyrimidin-4-yloxy]-piperidine-1-carboxylic acid isopropyl ester (cf Example 4.1 or 4.2 of WO 2007/035355), as well as pharmaceutically acceptable salts, solvates and hydrates thereof.

Particular reference is made to that GPR119 agonist of Formula (I) as shown in WO 2008/005569, i.e. 4-[5-methoxy-6-(2-methyl-6-[1,2,4]triazol-1-yl-pyridin-3-ylamino)-pyrimidin-4-yloxy]-piperidine-1-carboxylic acid isopropyl ester (cf Example 3.6 or 3.9 of WO 2008/005569), as well as pharmaceutically acceptable salts, solvates and hydrates thereof.

Particular reference is made to that GPR119 agonist of Formula (I) as shown in WO 2008/005576, i.e. 4-[6-(6-methanesulfonyl-2-methyl-pyridin-3-ylamino)-5-methyl-pyrimidin-4-yloxy]-piperidine-1-carboxylic acid isopropyl ester (cf Example 3.5 of WO 2008/005576), as well as pharmaceutically acceptable salts, solvates and hydrates thereof.

DPP-4 inhibitors and GPR119 agonists within the meaning of this invention include but are not limited to those described generically or specifically hereinbefore and hereinafter (including those described by reference to the herein-cited documents).

For avoidance of any doubt, the disclosure of each of the foregoing documents cited above is specifically incorporated herein by reference in its entirety.

Within the scope of the present invention it has now surprisingly been found that a combination of a DPP-4 inhibitor with a GPR119 agonist, each as defined herein, has surprising and particularly advantageous properties, which make this combination particularly suitable for treating and/or preventing (including preventing the progression) of metabolic diseases, particularly diabetes (especially type 2 diabetes mellitus) and conditions related thereto (e.g. diabetic complications).

Thus, the combinations according to the present invention may be useful in one or more of the following methods
- for preventing, slowing progression of, delaying, or treating a metabolic disorder;
- for improving glycemic control and/or for reducing of fasting plasma glucose, of postprandial plasma glucose and/or of glycosylated hemoglobin HbA1c;
- for preventing, slowing, delaying or reversing progression from impaired glucose tolerance, insulin resistance and/or from metabolic syndrome to type 2 diabetes mellitus;
- for preventing, slowing progression of, delaying or treating of a condition or disorder selected from the group consisting of complications of diabetes mellitus;
- for reducing the weight or preventing an increase of the weight or facilitating a reduction of the weight;
- for preventing or treating the degeneration of pancreatic beta cells and/or for improving and/or restoring the functionality of pancreatic beta cells and/or restoring the functionality of pancreatic insulin secretion; and/or
- for maintaining and/or improving the insulin sensitivity and/or for treating or preventing hyperinsulinemia and/or insulin resistance.

Further, the combinations according to the present invention may be useful in a method for increasing plasma GLP-1 levels.

Accordingly, examples of such metabolic diseases or disorders amenable to the therapy of this invention include, without being restricted to, Type 1 diabetes, Type 2 diabetes, inadequate glucose tolerance, insulin resistance, hyperglycemia, hyperlipidemia, hypercholesterolemia, dyslipidemia, syndrome X, metabolic syndrome, obesity, hypertension, chronic systemic inflammation, retinopathy, neuropathy, nephropathy, atherosclerosis, endothelial dysfunction and osteoporosis.

In a certain embodiment, the combinations of this invention may be useful for anti-diabetic therapy or prophylaxis in diabetic (especially obese) patients suffering from severe or highly insulin resistance.

Thus, the present invention provides a combination therapeutic product or a pharmaceutical composition comprising a DPP-4 inhibitor as defined herein and a GPR119 agonist as defined herein.

The present invention further provides a pharmaceutical combined preparation comprising a DPP-4 inhibitor as defined herein and a GPR119 agonist as defined herein.

Within this invention it is to be understood that the combinations or combined uses according to this invention envisage the simultaneous, sequential or separate administration of the components. It will be appreciated that the DPP-4 inhibitor and the GPR119 agonist can be administered in a single dosage form or each in separate dosage forms. When the DPP-4 inhibitor and the GPR119 agonist are in separate dosage forms, they can be administered by different routes. Where the administration of the active components is sequential or separate, the delay in administering the second component should preferably not be such as to lose the beneficial effect of the combination therapy. In this context, sequential administration may also include (without being limited to), for example, alternate administration of the active components.

Thus, for avoidance of any doubt, the present invention provides a combination therapeutic product or a pharmaceutical composition comprising a DPP-4 inhibitor as defined herein and a GPR119 agonist as defined herein, for simultaneous, sequential or separate use in the treatment or prevention of metabolic diseases, particularly type 2 diabetes mellitus and conditions related thereto.

The present invention further provides a pharmaceutical composition comprising a DPP-4 inhibitor as defined herein in combination with a GPR119 agonist as defined herein, and optionally one or more pharmaceutically acceptable carriers and/or diluents.

The present invention further provides a pharmaceutical composition which comprises a DPP-4 inhibitor as defined herein and a GPR119 agonist as defined herein, formulated altogether, in conjunction or as admixture with one or more inert diluents and/or carriers. Such a composition conveniently provides the combination therapeutic product of the invention for simultaneous or concurrent therapeutic use.

The present invention further provides a pharmaceutical composition comprising
a first composition comprising a DPP-4 inhibitor as defined herein and optionally one or more inert carriers and/or diluents, and
a second composition comprising a GPR119 agonist as defined herein and optionally one or more inert carriers and/or diluents.

Such a combination conveniently provides the combination therapeutic product of the invention for (chronologically) staggered, sequential or separate therapeutic use.

Conveniently, such a pharmaceutical composition of the invention comprises a kit-of-parts comprising a first container with a suitable composition comprising a DPP-4 inhibitor as defined herein and a second container with a suitable composition comprising a GPR119 agonist as defined herein, optionally together with instructions for simultaneous, sequential or separate use in therapy.

The compositions of the invention may be in a form suitable for oral use (e.g. as tablets, capsules, aqueous or oily suspensions, emulsions or dispersible powders or granules), for parenteral administration (e.g. as a sterile aqueous or oily solution or suspension for intravenous, subcutaneous, intramuscular or intravascular dosing), for topical use (e.g. as creams, gels or ointments) or as a suppository for rectal dosing. Preferably the compositions of the invention are in form suitable for oral dose, for example as tablets or capsules.

The compositions of DPP-4 inhibitor and the GPR119 agonist, either individually or in combination, may be obtained by conventional procedures using suitable conventional pharmaceutically acceptable diluents and/or carriers. Further details or features of these compositions and their preparation may be found in the disclosure of the present application (including the disclosures of the herein-mentioned references).

The present invention further provides the use of combination therapeutic product according to this invention for the manufacture of a medicament for treating and/or preventing metabolic diseases, particularly type 2 diabetes mellitus and conditions related thereto.

The present invention further provides the use of a DPP-4 inhibitor as defined herein and a GPR119 agonist as defined herein for the manufacture of a combination therapeutic product (e.g. a pharmaceutical composition for administering simultaneously, sequentially or separately) for treating and/or preventing metabolic diseases, particularly type 2 diabetes mellitus.

The present invention further provides a method of treating and/or preventing metabolic diseases, particularly type 2 diabetes mellitus, said method comprising simultaneously, sequentially or separately administering to a subject in need thereof an effective amount of a DPP-4 inhibitor as defined herein and an effective amount of a GPR 119 agonist as defined herein.

The present invention further provides a DPP-4 inhibitor as defined herein for use in combination with a GPR119 agonist as defined herein. The present invention further provides a GPR119 agonist as defined herein for use in combination with a DPP-4 inhibitor agonist as defined herein.

The present invention further provides a DPP-4 inhibitor in combination with a GPR119 agonist for use in the therapies described herein.

Other aspects of the present invention may become apparent to the skilled person from the foregoing and following remarks.

A DPP-4 inhibitor within the meaning of the present invention includes, without being limited to, any of those DPP-4 inhibitors mentioned hereinabove and hereinbelow, preferably orally active DPP-4 inhibitors.

A GPR119 agonist within the meaning of the present invention includes, without being limited to, any of those GPR119 agonists mentioned hereinabove and hereinbelow, preferably orally active GPR119 agonists.

A special DPP-4 inhibitor within the meaning of this invention may be such an oral DPP-4 inhibitor, which and whose active metabolites have preferably a relatively wide (e.g. about >100 fold) therapeutic window and/or, especially, that are primarily eliminated via hepatic metabolism or biliary excretion.

In a first embodiment (embodiment A), a DPP-4 inhibitor in the context of the present invention is any DPP-4 inhibitor of formula (I)

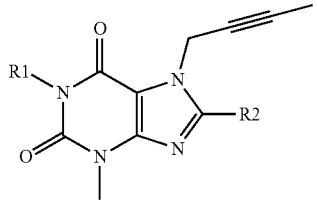

or formula (II)

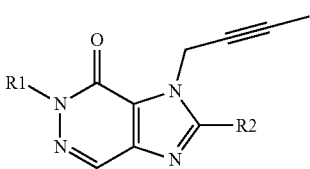

or formula (III)

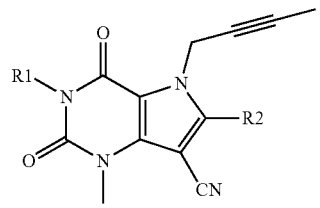

or formula (IV)

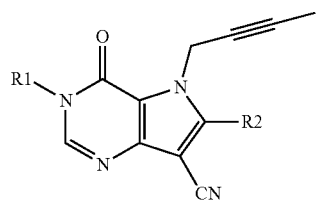

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino, or its pharmaceutically acceptable salt.

In a second embodiment (embodiment B), a DPP-4 inhibitor in the context of the present invention is a DPP-4 inhibitor selected from the group consisting of sitagliptin, vildagliptin, saxagliptin, alogliptin, (2S)-1-{[2-(5-Methyl-2-phenyl-oxazol-4-yl)-ethylamino]-acetyl}-pyrrolidine-2-carbonitrile, (2S)-1-{[1,1,-Dimethyl-3-(4-pyridin-3-yl-imidazol-1-yl)-propylamino]-acetyl}-pyrrolidine-2-carbonitrile, (S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one, (3,3-Difluoropyrrolidin-1-yl)-((2S,4S)-4-(4-(pyrimidin-2-yl)piperazin-1-yl)pyrrolidin-2-yl)methanone, (1((3S,4S)-4-amino-1-(4-(3,3-difluoropyrrolidin-1-yl)-1,3,5-triazin-2-yl)pyrrolidin-3-yl)-5,5-difluoropiperidin-2-one, (2S,4S)-1-{2-[(3S,1R)-3-(1H-1,2,4-Triazol-1-ylmethyl)cyclopentylamino]-acetyl}-4-fluoropyrrolidine-2-carbonitrile, (R)-2-[6-(3-Amino-piperidin-1-yl)-3-methyl-2,4-dioxo-3,4-dihydro-2H-pyrimidin-1-ylmethyl]-4-fluoro-benzonitrile, 5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide, 3-{(2S,4S)-4-[4-(3-Methyl-1-phenyl-1H-pyrazol-5-yl)piperazin-1-yl]pyrrolidin-2-ylcarbonyl}thiazolidine,

[(2R)-1-{[(3R)-pyrrolidin-3-ylamino]acetyl}pyrrolidin-2-yl]boronic acid,
(2S,4S)-1-[2-[(4-ethoxycarbonylbicyclo[2.2.2]oct-1-yl)amino]acetyl]-4-fluoropyrrolidine-2-carbonitrile,
2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile, and
6-[(3R)-3-amino-piperidin-1-yl]-5-(2-chloro-5-fluoro-benzyl)-1,3-dimethyl-1,5-dihydropyrrolo[3,2-d]pyrimidine-2,4-dione, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142)):

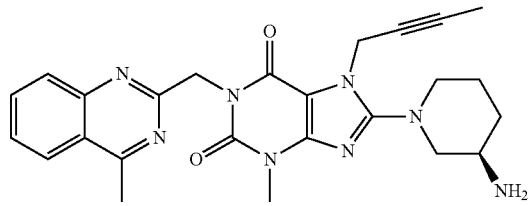 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252)):

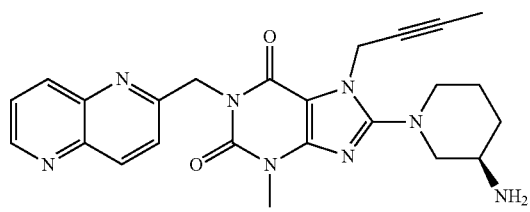 [SMILES: CC#CCn1c(N2CCC[C@@H](N)C2)nc2c1c(=O)n(Cc1ccc3ncccc3n1)c(=O)n2C]

1-[(Quinazolin-2-yl)methyl]-3-methyl-7-(2-butyn-1-yl)-8-((R)-3-amino-piperidin-1-yl)-xanthine (compare WO 2004/018468, example 2(80)):

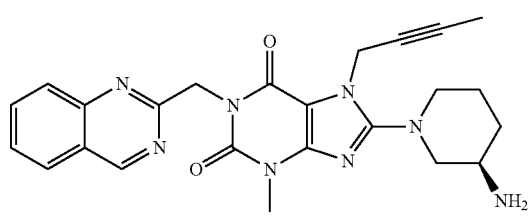 [SMILES: CC#CCn1c(N2CCC[C@@H](N)C2)nc2c1c(=O)n(Cc1ncc3ccccc3n1)c(=O)n2C]

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136):

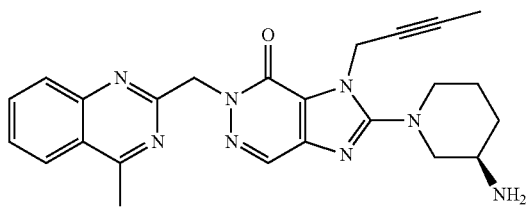 [SMILES: CC#CCn1c(N2CCC[C@@H](N)C2)nc2cnn(Cc3nc(C)c4ccccc4n3)c(=O)c21]

1-[(4-Methyl-quinazolin-2-yl)methyl]-3-methyl-7-(2-butyln-1-yl)-8-[(2-amino-2-methyl-propyl)-methylamino]-xanthine (compare WO 2006/029769, example 2(1)):

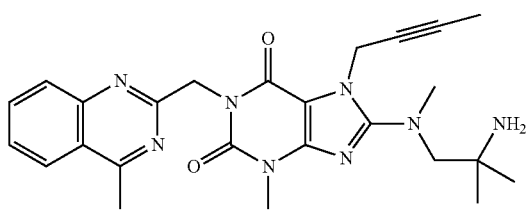 [SMILES: CC#CCn1c(N(C)CC(C)(C)N)nc2c1c(=O)n(Cc1nc(C)c3ccccc3n1)c(=O)n2C]

1-[(3-Cyano-quinolin-2-yl)methyl]-3-methyl-7-(2-butyn-1-yl)-8-((R)-3-amino-piperidin-1-yl)-xanthine (compare WO 2005/085246, example 1(30)):

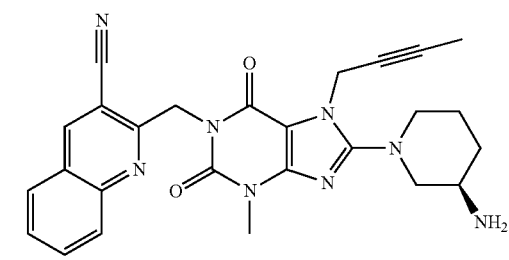 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39)):

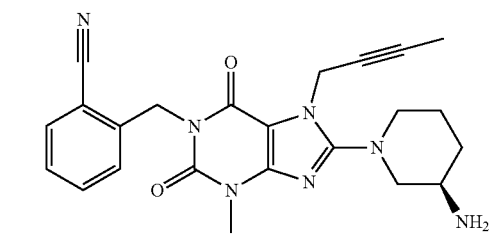 [SMILES: CC#CCn1c(N2CCC[C@@H](N)C2)nc2c1c(=O)n(Cc1ccccc1C#N)c(=O)n2C]

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4)):

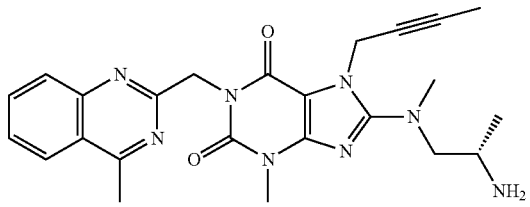 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52)):

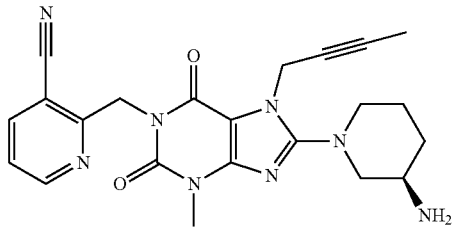 [SMILES: CC#CCn1c(N2CCC[C@@H](N)C2)nc2c1c(=O)n(Cc1ncccc1C#N)c(=O)n2C]

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81)):

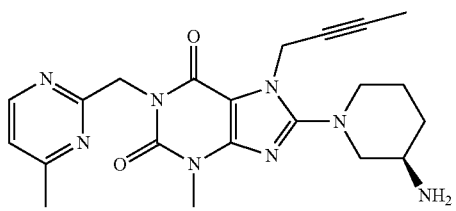 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82)):

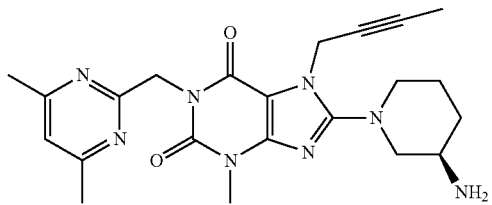 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(831):

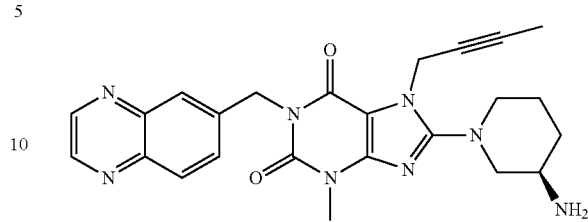

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as BI 1356), referred herein as "Cpd. A".

GPR119 agonists within the meaning of this invention may be selected from those compounds specifically described in the above-cited GPR119 agonist references (especially from those generic or specific compounds disclosed therein as preferred, or with specified activity data or with beneficial or useful effect), particularly from those species disclosed in those GPR119 agonist references to which particular reference is made herein, such as e.g. any GPR119 agonist selected from the left column of Table 1 as given later in this application.

Unless otherwise noted, according to this invention it is to be understood that the definitions of the active compounds (including the DPP-4 inhibitors and GPR119 agonists) mentioned hereinabove and hereinbelow also comprise their pharmaceutically acceptable salts as well as hydrates, solvates and polymorphic forms thereof. With respect to salts, hydrates and polymorphic forms thereof, particular reference is made to those which are referred to herein.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) and (IV) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith.

Polymorphous crystal modifications and formulations of particular DPP-4 inhibitors are disclosed in WO 2007/

128721 and WO 2007/128724, respectively, the disclosures of which are incorporated herein in their entireties. Formulations of particular DPP-4 inhibitors with metformin or other combination partners are described in PCT/EP2009053978, the disclosure of which is incorporated herein in its entirety. Typical dosage strengths of the dual combination of BI 1356/metformin are 2.5/500 mg, 2.5/850 mg and 2.5/1000 mg, each of which may be administered orally once or twice daily, in particular twice daily.

With respect to embodiment B, the methods of synthesis for the DPP-4 inhibitors of embodiment B are described in the scientific literature and/or in published patent documents, particularly in those cited herein.

For pharmaceutical application in warm-blooded vertebrates, particularly humans, the compounds of this invention are usually used in dosages from 0.001 to 100 mg/kg body weight, preferably at 0.1-15 mg/kg, in each case 1 to 4 times a day. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The pharmaceutical compositions according to this invention comprising the DPP-4 inhibitors as defined herein are thus prepared by the skilled person using pharmaceutically acceptable formulation excipients as described in the art. Examples of such excipients include, without being restricted to diluents, binders, carriers, fillers, lubricants, flow promoters, crystallisation retardants, disintegrants, solubilizers, colorants, pH regulators, surfactants and emulsifiers.

Examples of suitable diluents for compounds according to embodiment A include cellulose powder, calcium hydrogen phosphate, erythritol, low substituted hydroxypropyl cellulose, mannitol, pregelatinized starch or xylitol.

Examples of suitable lubricants for compounds according to embodiment A include talc, polyethyleneglycol, calcium behenate, calcium stearate, hydrogenated castor oil or magnesium stearate.

Examples of suitable binders for compounds according to embodiment A include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC).

Examples of suitable disintegrants for compounds according to embodiment A include corn starch or crospovidone.

Suitable methods of preparing pharmaceutical formulations of the DPP-4 inhibitors according to embodiment A of the invention are
  direct tabletting of the active substance in powder mixtures with suitable tabletting excipients;
  granulation with suitable excipients and subsequent mixing with suitable excipients and subsequent tabletting as well as film coating; or
  packing of powder mixtures or granules into capsules.
Suitable granulation methods are
  wet granulation in the intensive mixer followed by fluidised bed drying;
  one-pot granulation;
  fluidised bed granulation; or
  dry granulation (e.g. by roller compaction) with suitable excipients and subsequent tabletting or packing into capsules.

For details on dosage forms, formulations and administration of GPR119 agonists and DPP-4 inhibitors of this invention, reference is made to scientific literature and/or published patent documents, particularly to those cited herein.

For example, doses for the GPR119 agonists include, but not limited to, about 0.001 mg to about 25, 50, 100, 250, 500, 1000, 2500 or 5000 mg, conveniently be presented in a single dose or as divided doses administered at appropriate intervals, e.g. as two, three, four or more sub-doses per patient per day.

With respect to the first embodiment (embodiment A), the dosage typically required of the DPP-4 inhibitors mentioned herein in embodiment A when administered intravenously is 0.1 mg to 10 mg, preferably 0.25 mg to 5 mg, and when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, e.g. the dosage of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a DPP-4 inhibitor mentioned herein in embodiment A contain the active ingredient in a dosage range of 0.1-100 mg. Thus, e.g. particular dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg.

With respect to the second embodiment (embodiment B), the doses of DPP-4 inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single dosage strengths comprise, for example, 10, 25, 40, 50, 75, 100, 150 and 200 mg of the DPP-4 inhibitor active moiety.

A dosage strength of the DPP-4 inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure. Typical dosage strengths of the dual combination of sitagliptin/metformin are 50/500 mg and 50/1000 mg, each of which may be administered orally once or twice daily, in particular twice daily.

A dosage range of the DPP-4 inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin may be between 25 and 150 mg or between 50 and 100 mg. In another more particular aspect, the daily administration of vildagliptin may be 50 or 100 mg. The application of the active ingredient may occur up to three times a day, preferably one or two times a day. Particular dosage strengths are 50 mg or 100 mg vildagliptin. Typical dosage strengths of the dual combination of vildagliptin/metformin are 50/850 mg and 50/1000 mg, each of which may be administered orally once or twice daily, in particular twice daily.

Alogliptin may be administered to a patient at a daily dose of between 5 mg/day and 250 mg/day, optionally between 10 mg and 200 mg, optionally between 10 mg and 150 mg, and optionally between 10 mg and 100 mg of alogliptin (in each instance based on the molecular weight of the free base form of alogliptin). Thus, specific dosage amounts that may be used include, but are not limited to 10 mg, 12.5 mg, 20 mg, 25 mg, 50 mg, 75 mg and 100 mg of alogliptin per day. Alogliptin may be administered in its free base form or as a pharmaceutically acceptable salt.

Saxagliptin may be administered to a patient at a daily dose of between 2.5 mg/day and 100 mg/day, optionally between 2.5 mg and 50 mg. Specific dosage amounts that may be used include, but are not limited to 2.5 mg, 5 mg, 10 mg, 15 mg, 20 mg, 30 mg, 40 mg, 50 mg and 100 mg of saxagliptin per day. Typical dosage strengths of the dual combination of saxagliptin/metformin are 2.5/500 mg and 2.5/1000 mg, each of which may be administered orally once or twice daily, in particular twice daily.

A special embodiment of the DPP-4 inhibitors of this invention refers to those orally administered DPP-4 inhibitors which are therapeutically efficacious at low dose levels, e.g. at dose levels<100 mg or <70 mg per patient per day, preferably <50 mg, more preferably <30 mg or <20 mg, even more preferably from 1 mg to 10 mg per patient per day, particularly from 1 mg to 5 mg (more particularly 5 mg), per patient per day (if required, divided into 1 to 4 single doses, particularly 1 or 2 single doses, which may be of the same size), preferentially, administered orally once- or twice daily (more preferentially once-daily), advantageously administered at any time of day, with or without food. Thus, for example, the daily oral amount 5 mg BI 1356 can be given in a once daily dosing regimen (i.e. 5 mg BI 1356 once daily) or in a twice daily dosing regimen (i.e. 2.5 mg BI 1356 twice daily), at any time of day, with or without food.

A particularly preferred DPP-4 inhibitor to be emphasized within the meaning of this invention is 1-[(4-methyl-quinazolin-2-yl)methyl]-3-methyl-7-(2-butyn-1-yl)-8-(3-(R)-amino-piperidin-1-yl)-xanthine free base (also known as BI 1356). BI 1356 exhibits high potency, 24 h duration of action, and a wide therapeutic window. With low therapeutic doses of about >5 mg, BI 1356 acts as a true once-daily oral drug with a full 24 h duration of DPP-4 inhibition. At therapeutic oral dose levels, BI 1356 is mainly excreted via the liver and only to a minor extent (about <7% of the administered oral dose) via the kidney.

For illustrative example, the pharmaceutical compositions, methods and uses according to this invention relate to any of the combinations 1-15 as indicated in the following Table 1:

TABLE 1

| No. | GPR119 agonist | DPP-4 inhibitor |
|---|---|---|
| 1 | 4-[6-(6-methanesulfonyl-2-methyl-pyridin-3-ylamino)-5-methyl-pyrimidin-4-yloxy]-piperidine-1-carboxylic acid isopropyl ester | Cpd. A |
| 2 | 4-[5-methoxy-6-(2-methyl-6-[1,2,4]triazol-1-yl-pyridin-3-ylamino)-pyrimidin-4-yloxy]-piperidine-1-carboxylic acid isopropyl ester | Cpd. A |
| 3 | 4-[5-methyl-6-(2-methyl-pyridin-3-yloxy)-pyrimidin-4-yloxy]-piperidine-1-carboxylic acid isopropyl ester | Cpd. A |
| 4 | {6-[1-(3-isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine | Cpd. A |
| 5 | 4-[6-(6-methanesulfonyl-2-methyl-pyridin-3-ylamino)-5-methyl-pyrimidin-4-yloxy]-piperidine-1-carboxylic acid isopropyl ester | Cpd. A |
| 6 | 4-[6-(6-methanesulfonyl-4-methyl-pyridin-3-ylamino)-5-methoxy-pyrimidin-4-yloxy]-piperidine-1-carboxylic acid isopropyl ester | Cpd. A |
| 7 | 4-[6-(6-methanesulfonyl-2-methyl-pyridin-3-ylamino)-5-methoxy-pyrimidin-4-yloxy]-piperidine-1-carboxylic acid isopropyl ester | Cpd. A |
| 8 | (2-fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine | Cpd. A |
| 9 | 4-[1-(2-fluoro-4-methanesulfonyl-phenyl)-1H-pyrazolo[3,4-d]pyrimidin-4-yloxy]-piperidine-1-carboxylic acid isopropyl ester | Cpd. A |
| 10 | 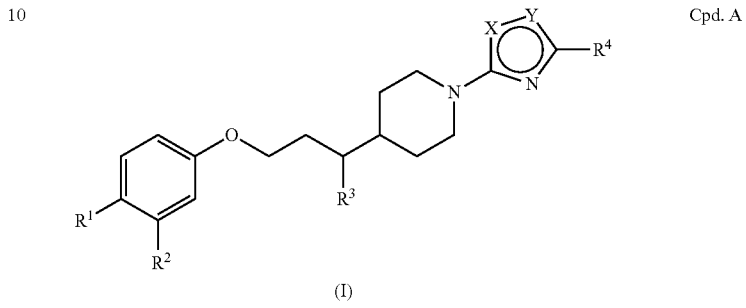 (I) | Cpd. A |

TABLE 1-continued

| No. | GPR119 agonist | DPP-4 inhibitor |
|---|---|---|
| | in which<br>one of X and Y is O and the other is N,<br>$R^1$ is —$SO_2C_{1-3}$alkyl, particularly —$SO_2CH_3$,<br>$R^2$ is H, F, Cl or $CH_3$, particularly H or F,<br>$R^3$ is H or $CH_3$, and<br>$R^4$ is $C_{2-5}$alkyl, e.g. $C_{3-4}$alkyl, particularly isopropyl. | |
| 11 | 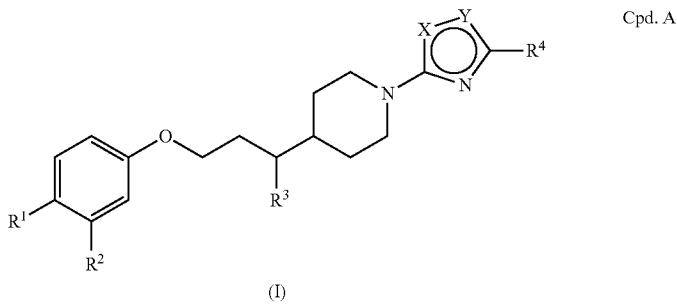<br>(I)<br>in which<br>one of X and Y is O and the other is N,<br>$R^1$ is —$CONHR^5$,<br>$R^2$ is H, F, Cl or $CH_3$,<br>$R^3$ is H or $CH_3$,<br>$R^4$ is $C_{2-5}$alkyl, e.g. $C_{3-4}$alkyl, particularly isopropyl, and<br>$R^5$ is H, $C_{1-3}$alkyl, or $C_{2-3}$alkyl substituted by hydroxy,<br>particularly 2-hydroxy-1-methylethyl. | Cpd. A |
| 12 | 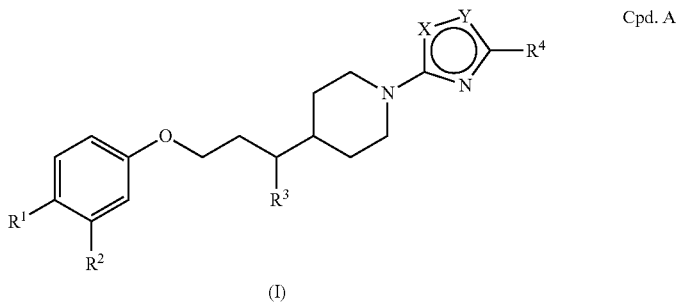<br>(I)<br>in which<br>one of X and Y is O and the other is N,<br>$R^1$ is —$CH_2$—$SO_2C_{1-3}$alkyl, particularly —$CH_2$—$SO_2CH_3$,<br>$R^2$ is H, F, Cl or $CH_3$, particularly F,<br>$R^3$ is H or $CH_3$, and<br>$R^4$ is $C_{2-5}$alkyl, e.g. $C_{3-4}$alkyl, particularly isopropyl. | Cpd. A |
| 13 | 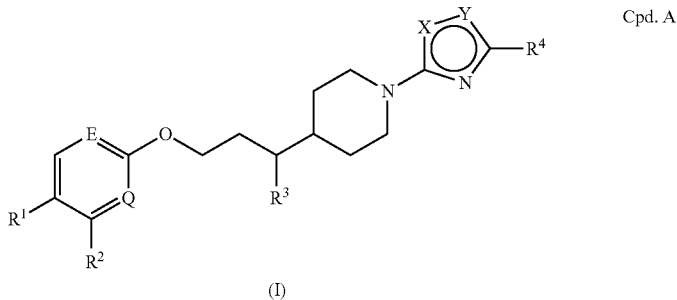<br>(I)<br>in which<br>one of X and Y is O and the other is N,<br>one of E and Q is N and the other is CH,<br>$R^1$ is —$SO_2R^5$, or —$CONHR^6$,<br>$R^2$ is H or $CH_3$,<br>$R^3$ is H or $CH_3$,<br>$R^4$ is $C_{2-5}$alkyl, e.g. $C_{3-4}$alkyl, particularly isopropyl,<br>$R^5$ is $C_{1-3}$alkyl, particularly $CH_3$, and<br>$R^6$ is H, $C_{1-3}$alkyl, or $C_{2-3}$alkyl substituted by hydroxy,<br>particularly 2-hydroxyethyl or 2-hydroxy-1-methylethyl. | Cpd. A |

TABLE 1-continued

| No. | GPR119 agonist | DPP-4 inhibitor |
|---|---|---|

14

*[Structure of Formula (I): a pyridine ring substituted with $R^1$, $R^2$, connected via O-CH$_2$-CH$_2$-CH($R^3$) to a piperidine, which is N-linked to a 5-membered heterocycle containing X, Y, N with $R^4$ substituent]*

Cpd. A (I)

in which
one of X and Y is O and the other is N,
$R^1$ is —SO$_2$R$^5$, —NR$^6$R$^7$ or —CONR$^6$R$^7$,
$R^2$ is H or CH$_3$,
$R^3$ is H or CH$_3$,
$R^4$ is C$_{2-5}$alkyl, e.g. C$_{3-4}$alkyl, particularly isopropyl,
$R^5$ is C$_{1-3}$alkyl, particularly CH$_3$,
$R^6$ is H, C$_{1-3}$alkyl, or C$_{2-3}$alkyl substituted by hydroxy,
particularly 2-hydroxyethyl or 2-hydroxy-1-methylethyl,
and
$R^7$ is hydrogen.

15

*[Structure: 5-ethyl-2-{4-[4-(4-tetrazol-1-yl-phenoxymethyl)-thiazol-2-yl]-piperidin-1-yl}-pyrimidine]*

Cpd. A 5-ethyl-2-{4-[4-(4-tetrazol-1-yl-phenoxymethyl)-thiazol-2-yl]-piperidin-1-yl}-pyrimidine having the formula As different metabolic functional disorders often occur simultaneously, it is quite often indicated to combine a number of different active principles with one another. Thus, depending on the functional disorders diagnosed, improved treatment outcomes may be obtained if a combination therapy of this invention is provided alone or combined with other active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The combination therapeutic product of this invention may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner(s) needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as GI 262570; PPAR-gamma antagonists; PPAR-gamma/alpha modulators such as tesaglitazar, muraglitazar, aleglitazar, indeglitazar, AVE0897 and KRP297; PPAR-gamma/alpha/delta modulators; AMPK-activators such as AICAR; acetyl-CoA carboxylase (ACC1 and ACC2) inhibitors; diacylglycerol-acetyltransferase (DGAT) inhibitors; pancreatic beta cell GCRP agonists other than GPR119 agonists; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin zinc suspension and insulin glargin; Gastric inhibitory Peptide (GIP); pramlintide, davalintide; amylin and amylin analogues or GLP-1 and GLP-1 analogues such as Exendin-4, e.g. exenatide, exenatide LAR, liraglutide, taspoglutide, AVE-0010, LY-2428757, LY-2189265, semaglutide or albiglutide; SGLT2-inhibitors such as KGT-1251; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors, such as e.g. dapagliflozin, sergliflozin, atigliflozin, larnagliflozin or canagliflozin (or compound of formula (I-S) or (I-K) from WO 2009/035969); KV 1.3 channel inhibitors; GPR40 modulators; SCD-1 inhibitors; dopamine receptor agonists (bromocriptine mesylate [Cycloset]); and CCR-2 antagonists.

Metformin is usually given in doses varying from about 250 mg to 3000 mg, particularly from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day.

Particular dosage strengths may be 250, 500, 625, 750, 850 and 1000 mg of metformin hydrochloride.

A dosage of the partner drug pioglitazone is usually of about 1-10 mg, 15 mg, 30 mg, or 45 mg once a day.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib); LDL receptor modulators; and ApoB100 antisense RNA.

A dosage of the partner drug atorvastatin is usually from 1 mg to 40 mg or 10 mg to 80 mg once a day Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan and eprosartan.

A dosage of the partner drug telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apo-lipoprotein A-I.

Examples of combination partners for the treatment of obesity are sibutramine; tetrahydrolipstatin (orlistat), cetilistat; alizyme; dexfenfluramine; axokine; cannabinoid receptor 1 antagonists such as the CB1 antagonist rimonobant; MCH-1 receptor antagonists; MC4 receptor agonists; NPY5 as well as NPY2 antagonists; beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/metreleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

Assays for identifying a compound as a GPR119 agonist or DPP-4 inhibitor are known to the skilled person or are apparent from the herein-cited references.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Pharmacological Examples

The following examples show the beneficial effect on glycemic control or plasma GLP-1 levels of the combination of a DPP-4 inhibitor and various GPR119 agonists according to the present invention as compared to the respective monotherapies. All experimental protocols concerning the use of laboratory animals are reviewed by a federal Ethics Committee and approved by governmental authorities.

1$^{st}$ Example

According to a first example an oral glucose tolerance test is performed in overnight fasted 9-weeks old male Zucker Diabetic Fatty (ZDF) rats (ZDF/Crl-Lepr$^{fa}$). A pre-dose blood sample is obtained by tail bleed. Blood glucose is measured with a glucometer, and the animals are randomized for blood glucose (n=5/group). Subsequently, the groups receive a single oral administration of either vehicle alone (0.5% aqueous hydroxyethylcellulose containing 3 mM HCl) or vehicle containing either the GPR119 agonist or the DPP-4 inhibitor or the combination of the GPR119 agonist with the DPP-4 inhibitor. The animals receive an oral glucose load (2 g/kg) 30 min after compound administration. Blood glucose is measured in tail blood 15 min, 30 min, 60 min, and 90 min after the glucose challenge. Glucose excursion is quantified by calculating the reactive glucose AUC. The data are presented as mean±SEM. The two-sided unpaired Student t-test is used for statistical comparison of the control group and the active groups as well as between active groups.

Figure 1:
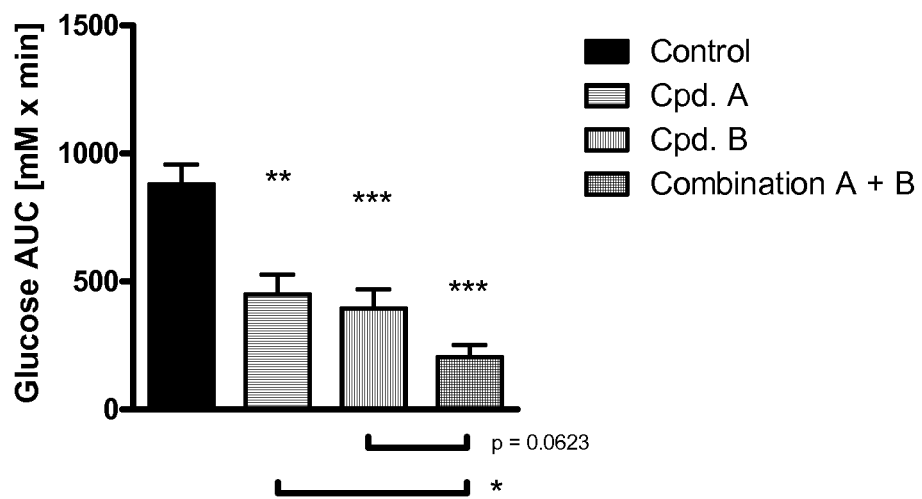
FIG. 1 shows glucose AUC in an oral glucose tolerance test performed in overnight fasted 9-weeks old male ZDF rats treated with control (vehicle), Cpd. A (DPP-4 inhibitor, 1-[(4-methyl-quinazolin-2-yl)methyl]-3-methyl-7(2-butyn-1-yl)-8-(3-(R)-amino-piperidin-1-yl)-xanthine), Cpd. B (GPR119 agonist, 4-(3-pyridin-4-yl-[1,2,4]oxadiazol-5-ylmethoxy)piperidine-1-carboxylic acid tert-butyl ester), and combination of Cpd. A + Cpd. B.

The result is shown in FIG. 1: "Cpd. A" is as defined herein (DPP-4 inhibitor) at a dose of 3 mg/kg. "Cpd. B" is 4-(3-pyridin-4-yl-[1,2,4]oxadiazol-5-ylmethoxy)piperidine-1-carboxylic acid tert-butyl ester (GPR119 agonist, Example 1 of WO 2005/061489) at a dose of 100 mg/kg. "Combination A+B" is the combination of said DPP-4 inhibitor and said GPR119 agonist at the same doses as in the respective monotherapies. P values versus control are indicated by symbols above the bars (*, p<0.05; , p<0.01; *, p<0.001). P values of the combination versus the monotherapies are indicated below the figure (*, p<0.05). The DPP-4 inhibitor reduces glucose excursion by 49%, the GPR119 agonist reduces glucose excursion by 55%. The combination decreased glucose excursion in the oral glucose tolerance test by 77%, and this reduction in glucose AUC is statistically significant versus DPP-4 inhibitor monotherapy.

2$^{nd}$ Example

According to a second example an oral glucose tolerance test is performed in overnight fasted 15-weeks old male Zucker Diabetic Fatty (ZDF) rats (ZDF/Crl-Lepr$^{fa}$). This aged ZDF rats serve as a highly insulin-resistant animal model. A pre-dose blood sample is obtained by tail bleed. Blood glucose is measured with a glucometer, and the animals are randomized for blood glucose (n=5/group). Subsequently, the groups receive a single oral administration of either vehicle alone (0.5% aqueous hydroxyethylcellulose containing 3 mM HCl) or vehicle containing either the GPR119 agonist or the DPP-4 inhibitor or the combination of the GPR119 agonist with the DPP-4 inhibitor. The animals receive an oral glucose load (2 g/kg) 30 min after compound administration. Blood glucose is measured in tail blood 30 min, 60 min, 90 min, 120 min, and 180 min after the glucose challenge. Glucose excursion is quantified by calculating the reactive glucose AUC. The data are presented as mean±SEM. The two-sided unpaired Student t-test is used for statistical comparison of the control group and the active groups as well as between active groups.

Figure 2:
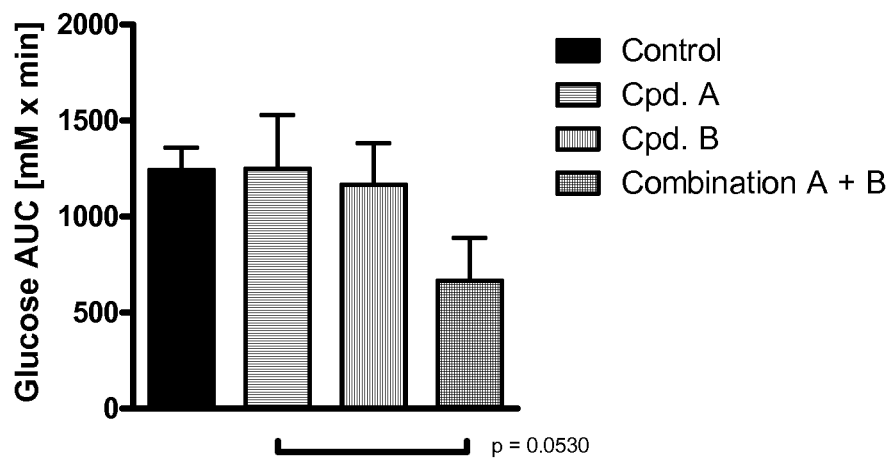
FIG. 2 shows glucose AUC in an oral glucose tolerance test performed in overnight fasted 15-weeks old male ZDF rats treated with control (vehicle), Cpd. A (DPP-4 inhibitor, 1-[(4-methyl-quinazolin-2-yl)methyl]-3-methyl-7-(2-butyn-1-yl)-8-(3-(R)-amino-piperidin-1-yl)-xanthine), Cpd. B (GPR119 agonist, (2-fluoro-4-methanesulfonyl-phenyl)-{6-[4-(3-isopropyl-[1,2,4]oxadiazol-5-yl)-piperidin-1-yl]-5-nitro-pyrimidin-4-yl}-amine), and combination of Cpd. A + Cpd. B.

The result is shown in FIG. 2: "Cpd. A" is as defined herein at a dose of 3 mg/kg. "Cpd. B" is (2-fluoro-4-methanesulfonyl-phenyl)-{6-[4-(3-isopropyl-[1,2,4]oxadiazol-5-yl)-piperidin-1-yl]-5-nitro-pyrimidin-4-yl}-amine (GPR119 agonist, WO 2004/065380) at a dose of 30 mg/kg. "Combination A+B" is the combination of said DPP-4 inhibitor and said GPR119 agonist at the same doses as in the respective monotherapies. The DPP-4 inhibitor reduces glucose excursion by 1%, the GPR119 agonist reduces glucose excursion by 6%. The combination decreased glucose excursion in the oral glucose tolerance test synergistically by 47%, and this reduction in glucose AUC reaches nearly statistically significance (p=0.0530) versus DPP-4 inhibitor monotherapy.

3$^{rd}$ Example

In a third example the same experimental setting is employed as in the second example as described herein before.

Figure 3:
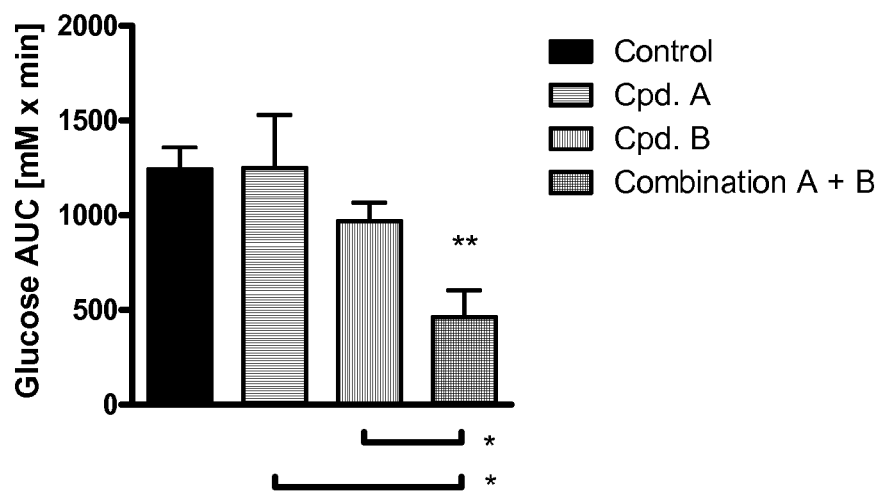
FIG. 3 shows glucose AUC in an oral glucose tolerance test performed in overnight fasted 15-weeks old male ZDF rats treated with control (vehicle), Cpd. A (DPP-4 inhibitor, 1-[(4-methyl-quinazolin-2-yl)methyl]-3-methyl-7-(2-butyn-1-yl)-8-(3-(R)-amino-piperidin-1-yl)-xanthine), Cpd. B (GPR119 agonist, 4-[5-methyl-6-(2-methyl-pyridin-3-yloxy)-pyrimidin-4-yloxy]-piperidine-1-carboxylic acid isopropyl ester), and combination of Cpd. A + Cpd. B.

The result is shown in FIG. 3: "Cpd. A" is as defined herein (DPP-4 inhibitor) at a dose of 3 mg/kg. "Cpd. B" is 4-[5-methyl-6-(2-methyl-pyridin-3-yloxy)-pyrimidin-4-yloxy]-piperidine-1-carboxylic acid isopropyl ester (GPR119 agonist, WO 2007/035355) at a dose of 10 mg/kg. "Combination A+B" is the combination of said DPP-4 inhibitor and said GPR119 agonist at the same doses as in the respective monotherapies. P values versus control are indicated by symbols above the bars (**, p<0.01). P values of the combination versus the monotherapies are indicated below the figure (*, p<0.05). The DPP-4 inhibitor reduces glucose excursion by 1%, the said GPR119 agonist reduces glucose excursion by 22%. The combination decreased glucose excursion in the oral glucose tolerance test synergistically by 63%, and this reduction in glucose AUC is statistically significant versus DPP-4 inhibitor monotherapy and GPR119 agonist monotherapy.

4$^{th}$ Example

In a fourth example the plasma GLP-1 profile is measured in a meal tolerance test. Therefore, overnight fasted male Sprague Dawley rats (Crl:CD(SD)) with a body weight of about 220 g are used (n=5/group). Blood samples are obtained by retroorbital puncture in vials containing a DPP-4 inhibitor and a protease inhibitor. GLP-1 is measured with a commercially available test kit (Linco research). A pre-dose blood sampling is done 1 h before refeeding. Subsequently, the groups receive a single oral administration of either vehicle alone (0.5% aqueous hydroxyethylcellulose containing 3 mM HCl) or vehicle containing either the GPR119 agonist or the DPP-4 inhibitor or the combination of the GPR119 agonist with the DPP-4 inhibitor. The animals are refed 30 min after compound administration. Plasma GLP-1 is measured 0.5 h, 1 h, 3 h, and 5 h after refeeding. The data are presented as mean±S.E.M. Statistical comparisons are conducted by Student's t test.

Figure 4:
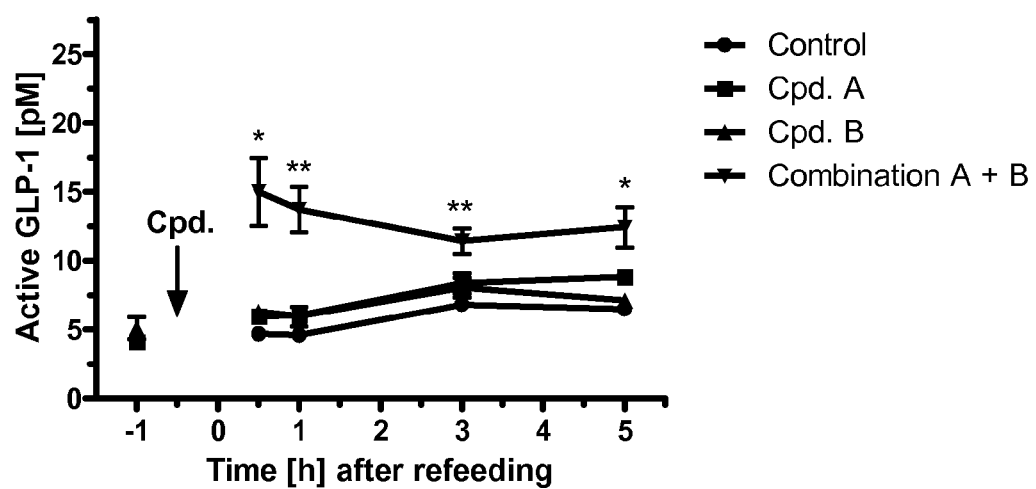
FIG. 4 shows active GLP-1 profile in a meal tolerance test performed in overnight fasted male SD rats treated with control (vehicle), Cpd. A (DPP-4 inhibitor, 1-[(4-methyl-quinazolin-2-yl)methyl]-3-methyl-7-(2-butyn-1-yl)-8-(3-(R)-amino-piperidin-1-yl)-xanthine), Cpd. B (GPR119 agonist, (2-fluoro-4-methanesulfonyl-phenyl)-{6-[4-(3-isopropyl-[1,2,4]oxadiazol-5-yl)-piperidin-1-yl]-5-nitro-pyrimidin-4-yl}-amine), and combination of Cpd. A + Cpd. B.

The result is shown in FIG. 4: "Cpd. A" is as defined herein (DPP-4 inhibitor) at a dose of 3 mg/kg. "Cpd. B" is (2-fluoro-4-methanesulfonyl-phenyl)-{6-[4-(3-isopropyl-[1,2,4]oxadiazol-5-yl)-piperidin-1-yl]-5-nitro-pyrimidin-4-yl}-amine (GPR119 agonist, WO 2004/065380) at a dose of 30 mg/kg. "Combination A+B" is the combination of said DPP-4 inhibitor and said GPR119 agonist at the same doses as in the respective monotherapies. The combination significantly increases plasma GLP-1 in the meal tolerance test as compared to the respective monotherapies. P values versus control are indicated by symbols (*, $p<0.05$; **, $p<0.01$).

5$^{th}$ Example

In a fifth example the same experimental setting is employed as in the fourth example as described herein before.

Figure 5:
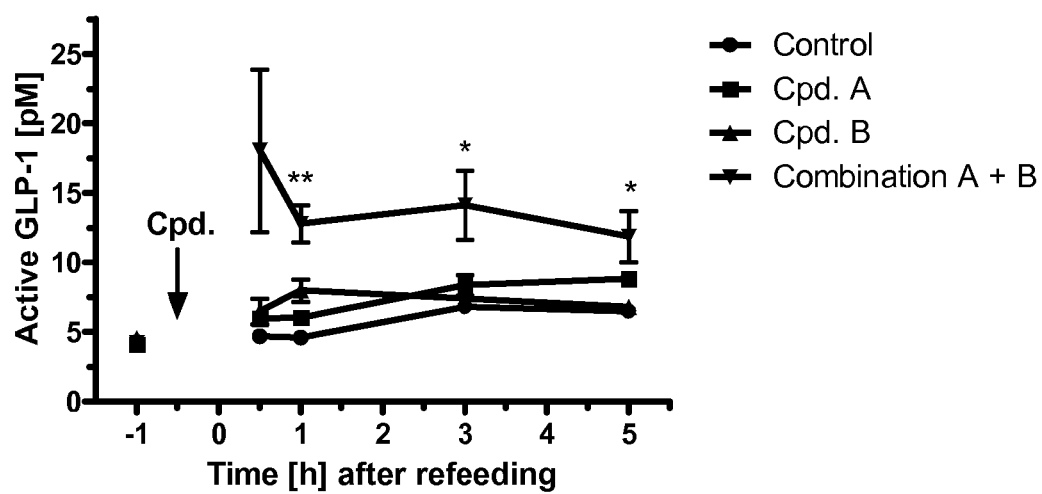
FIG. 5 shows active GLP-1 profile in a meal tolerance test performed in overnight fasted male SD rats treated with control (vehicle), Cpd. A (DPP-4 inhibitor, 1-[(4-methyl-quinazolin-2-yl)methyl]-3-methyl-7-(2-butyn-1-yl)-8-(3-(R)-amino-piperidin-1-yl)-xanthine), Cpd. B (GPR119 agonist, 4-[5-methyl-6-(2-methyl-pyridin-3-yloxy)-pyrimidin-4-yloxy]-piperidine-1-carboxylic acid isopropyl ester), and combination of Cpd. A + Cpd. B.

The result is shown in FIG. 5: "Cpd. A" is as defined herein (DPP-4 inhibitor) at a dose of 3 mg/kg. "Cpd. B" is 4-[5-methyl-6-(2-methyl-pyridin-3-yloxy)-pyrimidin-4-yloxy]-piperidine-1-carboxylic acid isopropyl ester (GPR119 agonist, WO 2007/035355) at a dose of 10 mg/kg. "Combination A+B" is the combination of said DPP-4 inhibitor and said GPR119 agonist at the same doses as in the respective monotherapies. The combination significantly increases plasma GLP-1 in the meal tolerance test as compared to the respective monotherapies. P values versus control are indicated by symbols (*, $p<0.05$; **, $p<0.01$).

Examples of Formulations

The following examples of formulations, which may be obtained analogously to methods known in the art, serve to illustrate the present invention more fully without restricting it to the contents of these examples. The term "active substance" denotes one or more compounds, e.g. it denotes a DPP-4 inhibitor or a GPR119 agonist according to this invention or a combination of said active ingredients, for example selected from the combinations as listed in the Table 1. Additional formulations particularly suitable for the DPP-4 inhibitor linagliptin may be those formulations disclosed in the application WO 2007/128724, the disclosure of which is incorporated herein in its entirety. Additional suitable formulations for the other compounds may be those formulations which are available on the market, or formulations described in the patent applications cited herein, or those described in the literature, for example as disclosed in current issues of "Rote Liste®" (Germany) or of "Physician's Desk Reference".

Example 1

Dry Ampoule Containing 75 mg of Active Substance Per 10 ml

Composition:

| Active substance | 75.0 mg |
|---|---|
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

Example 2

Dry Ampoule Containing 35 mg of Active Substance Per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

Example 3

Tablet Containing 50 mg of Active Substance

Composition:

| (1) Active substance | 50.0 mg |
|---|---|
| (2) Mannitol | 98.0 mg |
| (3) Maize starch | 50.0 mg |
| (4) Polyvinylpyrrolidone | 15.0 mg |
| (5) Magnesium stearate | 2.0 mg |
|  | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

Example 4

Tablet Containing 350 mg of Active Substance

Preparation:

| (1) Active substance | 350.0 mg |
|---|---|
| (2) Mannitol | 136.0 mg |
| (3) Maize starch | 80.0 mg |
| (4) Polyvinylpyrrolidone | 30.0 mg |
| (5) Magnesium stearate | 4.0 mg |
|  | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example 5

Capsules Containing 50 mg of Active Substance

Composition:

| | | |
|---|---|---|
| (1) Active substance | 50.0 mg | |
| (2) Dried maize starch | 58.0 mg | |
| (3) Mannitol | 50.0 mg | |
| (4) Magnesium stearate | 2.0 mg | |
| | 160.0 mg | |

Preparation:

(1) is triturated with (3). This trituration is added to the mixture of (2) and (4) with vigorous mixing. This powder mixture is packed into size 3 hard gelatin capsules in a capsule filling machine.

Example 6

Capsules Containing 350 mg of Active Substance

Composition:

| | | |
|---|---|---|
| (1) Active substance | 350.0 mg | |
| (2) Dried maize starch | 46.0 mg | |
| (3) Mannitol | 30.0 mg | |
| (4) Magnesium stearate | 4.0 mg | |
| | 430.0 mg | |

Preparation:

(1) is triturated with (3). This trituration is added to the mixture of (2) and (4) with vigorous mixing. This powder mixture is packed into size 0 hard gelatin capsules in a capsule filling machine.

The invention claimed is:

1. A pharmaceutical composition comprising:

(a) a GPR119 agonist of formula (10)

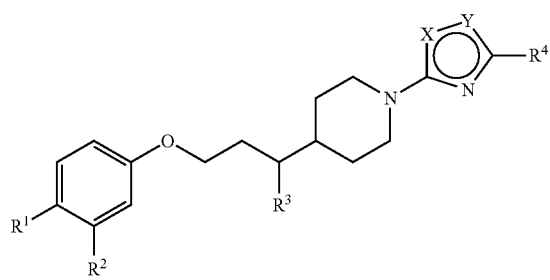

(10), wherein one of X and Y is O and the other is N, $R^1$ is —$SO_2$—$C_{1-3}$alkyl, $R^2$ is H, F, Cl, or $CH_3$, $R^3$ is H or $CH_3$, and $R^4$ is $C_{2-5}$alkyl;

formula (11)

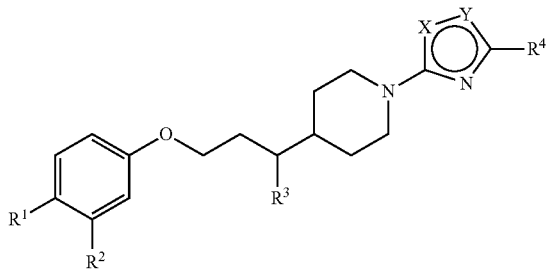

(11), wherein one of X and Y is O and the other is N, $R^1$ is —$CONHR^5$, $R^2$ is H, F, Cl, or $CH_3$, $R^3$ is H or $CH_3$, $R^4$ is $C_{2-5}$alkyl, and $R^5$ is H, $C_{1-3}$alkyl, or $C_{2-3}$alkyl substituted by hydroxy, formula (12)

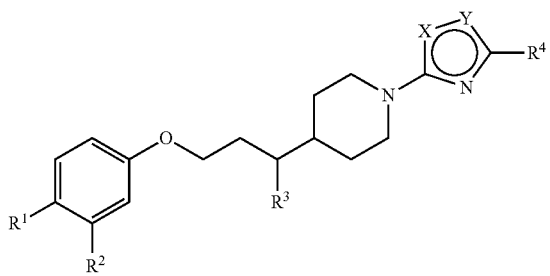

(12), wherein one of X and Y is O and the other is N, $R^1$ is —$CH_2$—$SO_2C_{1-3}$alkyl, $R^2$ is H, F, Cl, or $CH_3$, $R^3$ is H or $CH_3$, and $R^4$ is $C_{2-5}$alkyl;

formula (13)

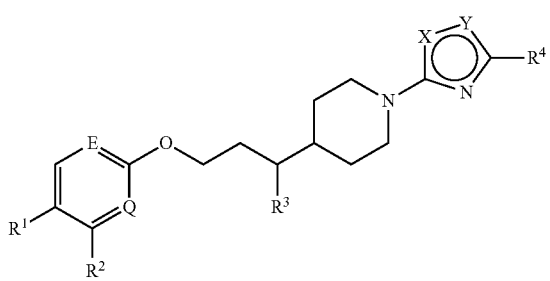

(13), wherein one of X and Y is O and the other is N, one of E and Q is N and the other is CH, $R^1$ is —$SO_2R^5$ or —$CONHR^6$, $R^2$ is H or $CH_3$, $R^3$ is H or $CH_3$, $R^4$ is $C_{2-5}$alkyl, $R^5$ is $C_{1-3}$alkyl, and $R^6$ is H, $C_{1-3}$alkyl, or $C_{2-3}$alkyl substituted by hydroxy;

formula (14)

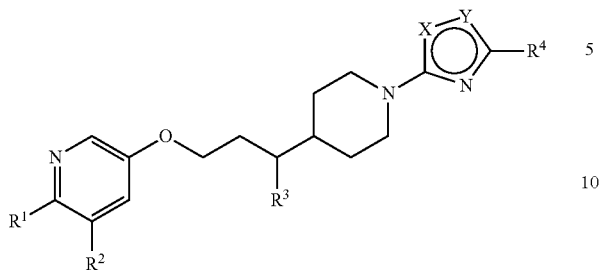

(14), wherein one of X and Y is O and the other is N, $R^1$ is —$SO_2R^5$, —$NR^6R^7$, or —$CONR^6R^7$, $R^2$ is H or $CH_3$, $R^3$ is H or $CH_3$, $R^4$ is $C_{2-5}$alkyl, $R^5$ is $C_{1-3}$alkyl, $R^6$ is H, $C_{1-3}$alkyl, or $C_{2-3}$alkyl substituted by hydroxy, and $R^7$ is hydrogen, or formula (15)

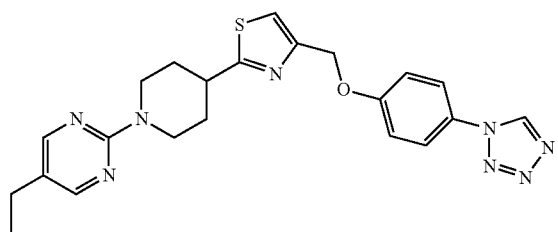 [SMILES: CCc1cnc(N2CCC(c3nc(COc4ccc(-n5cnnn5)cc4)cs3)CC2)nc1]

(15), 5-ethyl-2-{4-[4-(4-tetrazol-1-yl-phenoxymethyl)-thiazol-2-yl]-piperidin-1-yl}-pyrimidine, or a pharmaceutically acceptable salt thereof; and (b) a DPP-4 inhibitor of formula (I)

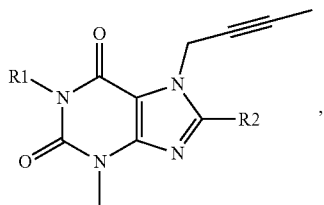

formula (II)

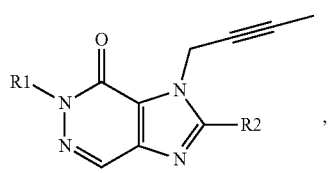

formula (III)

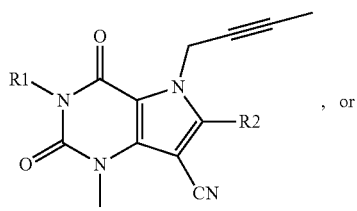

, or formula (IV)

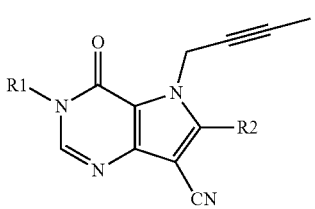

wherein:

R1 is ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl; and R2 is 3-(R)-amino-piperidin-1-yl, (2-amino-2-methyl-propyl)-methylamino, or (2-(S)-amino-propyl)-methylamino, or a pharmaceutically acceptable salt thereof.

2. The pharmaceutical composition according to claim 1, wherein the DPP-4 inhibitor is selected from the group consisting of 1-[(4-methyl-quinazolin-2-yl)methyl]-3-methyl-7-(2-butyn-1-yl)-8-(3-(R)-amino-piperidin-1-yl)-xanthine, 1-[([1,5]naphthyridin-2-yl)methyl]-3-methyl-7-(2-butyn-1-yl)-8-((R)-3-amino-piperidin-1-yl)-xanthine, 1-[(quinazolin-2-yl)methyl]-3-methyl-7-(2-butyn-1-yl)-8-((R)-3-amino-piperidin-1-yl)-xanthine, 2-((R)-3-amino-piperidin-1-yl)-3-(but-2-ynyl)-5-(4-methyl-quinazolin-2-ylmethyl)-3,5-dihydro-imidazo[4,5-d]pyridazin-4-one, 1-[(4-methyl-quinazolin-2-yl)methyl]-3-methyl-7-(2-butyn-1-yl)-8-[(2-amino-2-methyl-propyl)-methylamino]-xanthine, 1-[(3-cyano-quinolin-2-yl)-methyl]-3-methyl-7-(2-butyn-1-yl)-8-((R)-3-amino-piperidin-1-yl)-xanthine, 1-(2-cyano-benzyl)-3-methyl-7-(2-butyn-1-yl)-8-((R)-3-amino-piperidin-1-yl)-xanthine, 1-[(4-methyl-quinazolin-2-yl)-methyl]-3-methyl-7-(2-butyn-1-yl)-8-[(S)-(2-amino-propyl)-methylamino]-xanthine, 1-[(3-cyano-pyridin-2-yl)-methyl]-3-methyl-7-(2-butyn-1-yl)-8-((R)-3-amino-piperidin-1-yl)-xanthine, 1-[(4-methyl-pyrimidin-2-yl)-methyl]-3-methyl-7-(2-butyn-1-yl)-8-((R)-3-amino-piperidin-1-yl)-xanthine, 1-[(4,6-dimethyl-pyrimidin-2-yl)-methyl]-3-methyl-7-(2-butyn-1-yl)-8-((R)-3-amino-piperidin-1-yl)-xanthine; and 1-[(quinoxalin-6-yl)-methyl]-3-methyl-7-(2-butyn-1-yl)-8-((R)-3-amino-piperidin-1-yl)-xanthine, or a pharmaceutically acceptable salt thereof.

3. The pharmaceutical composition according to claim 1, wherein the DPP-4 inhibitor is 1-[(4-methyl-quinazolin-2-yl)-methyl]-3-methyl-7-(2-butyn-1-yl)-8-(3-(R)-amino-piperidin-1-yl)-xanthine.

4. The pharmaceutical composition according to claim 1, wherein the GPR119 agonist is the GPR119 agonist of formula (10)
or a pharmaceutically acceptable salt thereof.

5. A method of
preventing, slowing progression, delaying, or treating a metabolic disorder;
improving glycemic control and/or for reducing fasting plasma glucose, postprandial plasma glucose, and/or glycosylated hemoglobin HbA1c;
preventing, slowing, delaying, or reversing progression from impaired glucose tolerance, insulin resistance, and/or metabolic syndrome to type 2 diabetes mellitus;
preventing, slowing progression, delaying, or treating complications of diabetes mellitus;
reducing, preventing an increase, of the weight or facilitating a reduction of weight;
preventing or treating the degeneration of pancreatic beta cells and/or for improving and/or restoring the functionality of pancreatic beta cells and/or restoring the functionality of pancreatic insulin secretion; or
for maintaining and/or improving the insulin sensitivity and/or for treating or preventing hyperinsulinemia and/or insulin resistance,
the method comprising administering to a patient in need thereof the pharmaceutical composition of claim 1.

6. A method of lowering blood glucose level in a diabetic patients comprising administering to the patient a pharmaceutical composition of claim 1.

7. A method of improving glycemic control in a diabetic patients comprising administering to the patient a pharmaceutical composition of claim 1.

8. A method of improving glycemic control in the fasting and/or postprandial states in a diabetic patients comprising administering to the patient a pharmaceutical composition of claim 1.

9. A method of increasing plasma GLP-1 level in a diabetic patients comprising administering to the patient a pharmaceutical composition of claim 1.

10. A method of treating and/or preventing a disease, disorder, or condition responsive to the increase of plasma GLP-1 level in a patient in need thereof comprising administering to the patient a pharmaceutical composition of claim 1.

11. A method of improving glycemic control in highly insulin-resistant diabetic in a diabetic patients comprising administering to the patient a pharmaceutical composition of claim 1.

12. A method of treating and/or preventing Type 1 diabetes, Type 2 diabetes, inadequate glucose tolerance, insulin resistance, hyperglycemia, hyperlipidemia, hypercholesterolemia, dyslipidemia, syndrome X, metabolic syndrome, obesity, hypertension, chronic systemic inflammation, retinopathy, neuropathy, nephropathy, atherosclerosis, endothelial dysfunction, and/or osteoporosis in a patient in need thereof comprising administering to the patient a pharmaceutical composition of claim 1.

13. A method of reducing body weight or treating obesity in a patient in need thereof comprising administering to the patient a pharmaceutical composition of claim 1.

14. A method of treating dyslipidemia, hyperlipidemia, or hypercholesterolemia in a patient in need thereof comprising administering to the patient a pharmaceutical composition of claim 1.

15. A method of for treating metabolic syndrome (syndrome X) in a patient in need thereof comprising administering to the patient a pharmaceutical composition of claim 1.

16. The pharmaceutical composition according to claim 1, wherein the GPR119 agonist is the GPR119 agonist of formula (11) or a pharmaceutically acceptable salt thereof.

17. The pharmaceutical composition according to claim 1, wherein the GPR119 agonist is the GPR119 agonist of formula (12) or a pharmaceutically acceptable salt thereof.

18. The pharmaceutical composition according to claim 1, wherein the GPR119 agonist is the GPR119 agonist of formula (13) or a pharmaceutically acceptable salt thereof.

19. The pharmaceutical composition according to claim 1, wherein the GPR119 agonist is the GPR119 agonist of formula (14) or a pharmaceutically acceptable salt thereof.

20. The pharmaceutical composition according to claim 1, wherein the GPR119 agonist is the GPR119 agonist of formula (15) or a pharmaceutically acceptable salt thereof.

21. A kit comprising:
(a) a first pharmaceutical composition comprising a GPR119 agonist of formula (10)

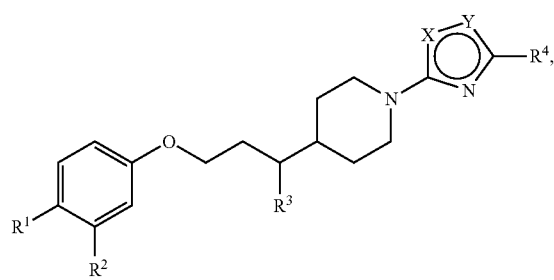

(10)

wherein one of X and Y is O and the other is N, $R^1$ is —$SO_2$—$C_{1-3}$alkyl, $R^2$ is H, F, Cl, or $CH_3$, $R^3$ is H or $CH_3$, and $R^4$ is $C_{2-5}$alkyl;

formula (11)

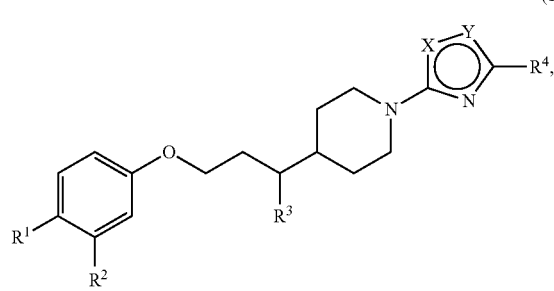

(11)

wherein one of X and Y is O and the other is N, $R^1$ is —$CONHR^5$, $R^2$ is H, F, Cl, or $CH_3$, $R^3$ is H or $CH_3$, $R^4$ is $C_{2-5}$alkyl, and $R^5$ is H, $C_{1-3}$alkyl, or $C_{2-3}$alkyl substituted by hydroxy, formula (12)

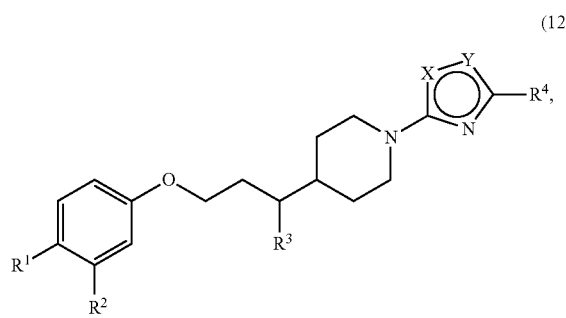

wherein one of X and Y is O and the other is N, $R^1$ is —$CH_2$—$SO_2C_{1-3}$alkyl, $R^2$ is H, F, Cl, or $CH_3$, $R^3$ is H or $CH_3$, and $R^4$ is $C_{2-5}$alkyl;

formula (13)

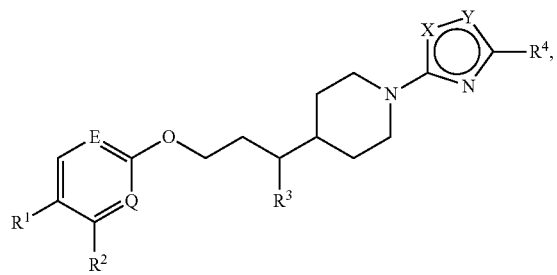

wherein one of X and Y is O and the other is N, one of E and Q is N and the other is CH, $R^1$ is —$SO_2R^5$ or —$CONHR^6$, $R^2$ is H or $CH_3$, $R^3$ is H or $CH_3$, $R^4$ is $C_{2-5}$alkyl, $R^5$ is $C_{1-3}$alkyl, and $R^6$ is H, $C_{1-3}$alkyl, or $C_{2-3}$alkyl substituted by hydroxy;

formula (14)

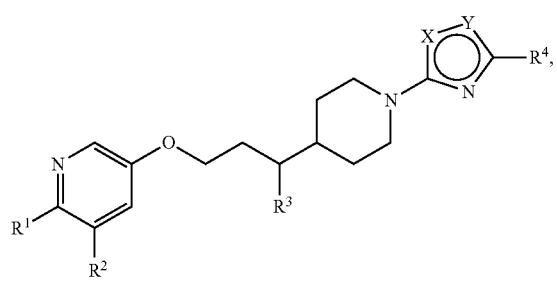

wherein one of X and Y is O and the other is N, $R^1$ is —$SO_2R^5$, —$NR^6R^7$, or —$CONR^6R^7$, $R^2$ is H or $CH_3$, $R^3$ is H or $CH_3$, $R^4$ is $C_{2-5}$alkyl, $R^5$ is $C_{1-3}$alkyl, $R^6$ is H, $C_{1-3}$alkyl, or $C_{2-3}$alkyl substituted by hydroxy, and $R^7$ is hydrogen, or formula (15)

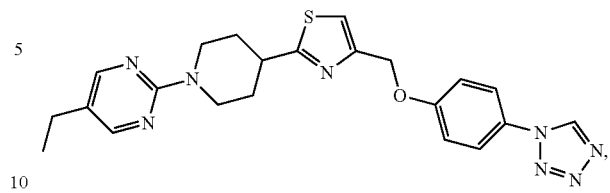

(15), 5-ethyl-2-{4-[4-(4-tetrazol-1-yl-phenoxymethyl)-thiazol-2-yl]-piperidin-1-yl}-pyrimidine,
or a pharmaceutically acceptable salt thereof; and
(b) a second pharmaceutical composition comprising a DPP-4 inhibitor of formula (I)

formula (I)

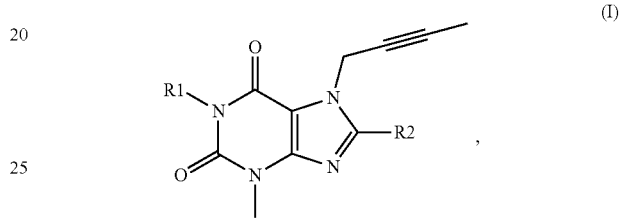

formula (II)

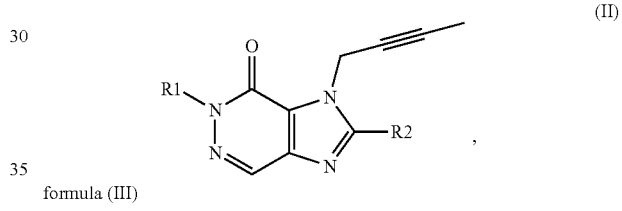

formula (III)

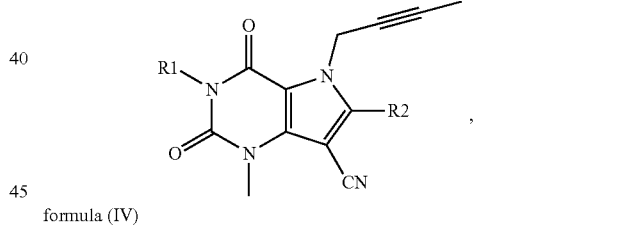

formula (IV)

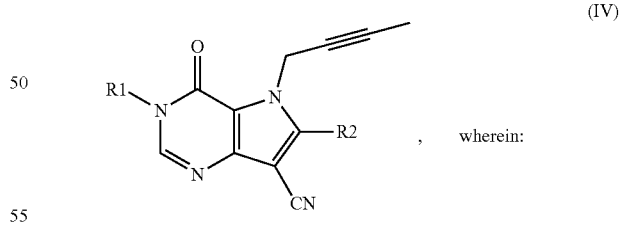

, wherein:

R1 is ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl; and R2 is 3-(R)-amino-piperidin-1-yl, (2-amino-2-methyl-propyl)-methylamino, or (2-(S)-amino-propyl)-methylamino, or a pharmaceutically acceptable salt thereof.

* * * * *